United States Patent
Mostafavi et al.

(10) Patent No.: US 10,667,727 B2
(45) Date of Patent: *Jun. 2, 2020

(54) SYSTEMS AND METHODS FOR DETERMINING A STATE OF A PATIENT

(75) Inventors: Hassan Mostafavi, Los Altos, CA (US); Sergey Povzner, Burlingame, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 1918 days.

This patent is subject to a terminal disclaimer.

(21) Appl. No.: 12/205,512

(22) Filed: Sep. 5, 2008

(65) Prior Publication Data
US 2010/0063419 A1    Mar. 11, 2010

(51) Int. Cl.
| | | |
|---|---|---|
| A61B 5/11 | (2006.01) | |
| A61B 6/00 | (2006.01) | |
| A61B 5/113 | (2006.01) | |
| G06K 9/00 | (2006.01) | |
| A61B 90/00 | (2016.01) | |
| G06T 7/246 | (2017.01) | |
| A61B 5/00 | (2006.01) | |

(52) U.S. Cl.
CPC .......... *A61B 5/1135* (2013.01); *A61B 90/36* (2016.02); *G06K 9/0053* (2013.01); *G06T 7/248* (2017.01); *A61B 5/7285* (2013.01); *A61B 6/5288* (2013.01); *A61B 6/541* (2013.01); *A61B 90/361* (2016.02); *A61B 2090/364* (2016.02); *G06K 2209/05* (2013.01); *G06T 2207/30004* (2013.01)

(58) Field of Classification Search
None
See application file for complete search history.

(56) References Cited

U.S. PATENT DOCUMENTS

| | | |
|---|---|---|
| 3,800,125 A | 3/1974 | Cleary |
| 3,861,807 A | 1/1975 | Lescrenier |
| 3,871,360 A | 3/1975 | Van Horn et al. |
| 3,952,201 A | 4/1976 | Hounsfield |
| 3,974,386 A | 8/1976 | Mistretta et al. |
| 4,031,884 A | 6/1977 | Henzel |
| 4,262,306 A | 4/1981 | Renner |
| 4,289,142 A | 9/1981 | Kearns |
| 4,335,427 A | 6/1982 | Hunt et al. |
| 4,387,722 A | 6/1983 | Kearns |
| 4,463,425 A | 7/1984 | Hirano et al. |
| 4,545,384 A | 10/1985 | Kawachi |
| 4,663,591 A | 5/1987 | Pelc et al. |
| 4,672,651 A | 6/1987 | Horiba et al. |
| 4,686,999 A | 8/1987 | Snyder et al. |
| 4,710,717 A | 12/1987 | Pelc et al. |
| 4,727,882 A | 3/1988 | Schneider et al. |
| 4,802,486 A | 2/1989 | Goodman et al. |
| 4,853,771 A | 8/1989 | Witriol et al. |
| 4,855,910 A | 8/1989 | Bohning |
| 4,895,160 A | 1/1990 | Reents |
| 4,928,692 A | 5/1990 | Goodman et al. |
| 4,971,065 A | 11/1990 | Pearce |
| 4,994,965 A | 2/1991 | Crawford et al. |
| 5,051,903 A | 9/1991 | Pelc et al. |
| 5,080,100 A | 1/1992 | Trotel |
| 5,107,845 A * | 4/1992 | Guern ............... A61B 5/113 348/143 |
| 5,109,435 A | 4/1992 | Lo et al. |
| 5,134,472 A | 7/1992 | Abe |
| 5,150,426 A | 10/1992 | Bahn et al. |
| 5,199,424 A | 4/1993 | Sullivan et al. |
| 5,207,223 A | 5/1993 | Adler et al. |
| 5,239,591 A | 8/1993 | Ranganath |
| 5,262,945 A | 11/1993 | DeCarli et al. |
| 5,265,142 A | 11/1993 | Hsieh |
| 5,271,055 A | 12/1993 | Hsieh et al. |
| 5,279,309 A | 1/1994 | Taylor et al. |
| 5,285,786 A | 2/1994 | Fujii |
| 5,295,483 A | 3/1994 | Nowacki et al. |
| 5,315,630 A | 5/1994 | Sturm et al. |
| 5,363,844 A | 11/1994 | Riederer et al. |
| 5,377,681 A | 1/1995 | Drane |
| 5,389,101 A | 2/1995 | Heilbrun et al. |

(Continued)

FOREIGN PATENT DOCUMENTS

| | | |
|---|---|---|
| DE | 4341324 A1 | 6/1995 |
| DE | 19856467 | 5/2000 |

(Continued)

OTHER PUBLICATIONS

Adams, W.B. et al. "Correlator Compensation Requirements for Passive Time-Delay Estimation with Moving Source or Receivers" IEEE (Apr. 1980) ASSP-28(2):158-168.

(Continued)

*Primary Examiner* — Katherine D Salmon
(74) *Attorney, Agent, or Firm* — Vista IP Law Group, LLP

(57) ABSTRACT

A method of monitoring a patient includes obtaining a first image of an object, obtaining a second image of the object, determining a level of similarity between the first and second images, obtaining a third image of the object, determining a level of similarity between the first and third images, analyzing a time series of values that includes the determined level of similarity between the first and second images and the determined level of similarity between the first and third images, and determining a state of the patient based at least on a result of the act of analyzing.

29 Claims, 14 Drawing Sheets

(56) References Cited

U.S. PATENT DOCUMENTS

| | | |
|---|---|---|
| 5,394,875 A | 3/1995 | Lewis et al. |
| 5,396,875 A | 3/1995 | Kotwicki et al. |
| 5,446,548 A | 8/1995 | Gerig et al. |
| 5,448,548 A | 9/1995 | Taneya et al. |
| 5,482,042 A | 1/1996 | Fujita |
| 5,513,646 A | 5/1996 | Lehrman et al. |
| 5,515,849 A | 5/1996 | Murashita et al. |
| 5,522,382 A | 6/1996 | Sullivan et al. |
| 5,531,520 A | 7/1996 | Grimson et al. |
| 5,535,289 A | 7/1996 | Ito |
| 5,538,494 A | 7/1996 | Matsuda |
| 5,549,655 A | 8/1996 | Erickson |
| 5,565,777 A | 10/1996 | Kanayama et al. |
| 5,573,012 A | 11/1996 | McEwan |
| 5,582,182 A | 12/1996 | Hillsman |
| 5,588,430 A | 12/1996 | Bova et al. |
| 5,603,318 A | 2/1997 | Heilbrun et al. |
| 5,619,995 A | 4/1997 | Lobodzinski |
| 5,622,187 A | 4/1997 | Carol |
| 5,638,819 A | 6/1997 | Manwaring et al. |
| 5,662,111 A | 9/1997 | Cosman |
| 5,662,112 A | 9/1997 | Heid |
| 5,727,554 A | 3/1998 | Kalend et al. |
| 5,738,102 A | 4/1998 | Lemelson |
| 5,764,723 A | 6/1998 | Weinberger et al. |
| 5,771,310 A | 6/1998 | Vannah |
| 5,784,431 A | 7/1998 | Kalend et al. |
| 5,794,621 A | 8/1998 | Hogan et al. |
| 5,820,553 A | 10/1998 | Hughes |
| 5,823,192 A | 10/1998 | Kalend et al. |
| 5,828,770 A | 10/1998 | Leis et al. |
| 5,836,954 A | 11/1998 | Heilbrun et al. |
| 5,891,034 A | 4/1999 | Bucholz |
| 5,906,202 A | 5/1999 | Schuster et al. |
| 5,912,656 A | 6/1999 | Tham et al. |
| 5,924,989 A | 7/1999 | Polz |
| 5,954,647 A | 9/1999 | Bova et al. |
| 5,982,915 A | 11/1999 | Doi et al. |
| 5,991,356 A | 11/1999 | Horiuchi et al. |
| 5,993,390 A | 11/1999 | Savard et al. |
| 5,993,397 A | 11/1999 | Branson |
| 5,997,883 A | 12/1999 | Epstein et al. |
| 6,061,644 A | 5/2000 | Leis |
| 6,067,373 A | 5/2000 | Ishida et al. |
| 6,075,557 A | 6/2000 | Holliman et al. |
| 6,076,005 A | 6/2000 | Sontag et al. |
| 6,084,939 A | 7/2000 | Tamura |
| 6,088,488 A | 7/2000 | Hardy et al. |
| 6,125,166 A | 9/2000 | Takeo |
| 6,138,302 A | 10/2000 | Sashin et al. |
| 6,144,874 A | 11/2000 | Du |
| 6,144,875 A | 11/2000 | Schweikard et al. |
| 6,146,390 A | 11/2000 | Heilbrun et al. |
| 6,165,181 A | 12/2000 | Heilbrun et al. |
| 6,185,445 B1 | 2/2001 | Knuttel |
| 6,185,446 B1 | 2/2001 | Carlsen, Jr. |
| 6,198,959 B1 | 3/2001 | Wang |
| 6,216,029 B1 | 4/2001 | Paltieli |
| 6,259,943 B1 | 7/2001 | Cosman et al. |
| 6,266,443 B1 | 7/2001 | Vetro et al. |
| 6,269,140 B1 | 7/2001 | Takagi et al. |
| 6,272,368 B1 | 8/2001 | Alexandrescu |
| 6,296,613 B1 | 10/2001 | Emmenegger et al. |
| 6,300,974 B1 | 10/2001 | Viala et al. |
| 6,307,914 B1 | 10/2001 | Kunieda et al. |
| 6,333,991 B1 | 12/2001 | Schreiber et al. |
| 6,348,058 B1 | 2/2002 | Melkent et al. |
| 6,370,217 B1 | 4/2002 | Hu et al. |
| 6,370,417 B1 | 4/2002 | Horbaschek et al. |
| 6,375,612 B1 | 4/2002 | Guichon et al. |
| 6,398,739 B1 | 6/2002 | Sullivan et al. |
| 6,405,072 B1* | 6/2002 | Cosman ............... 600/426 |
| 6,434,215 B1 | 8/2002 | Cesmeli |
| 6,434,507 B1 | 8/2002 | Clayton et al. |
| 6,473,634 B1 | 10/2002 | Bami et al. |
| 6,473,635 B1 | 10/2002 | Rasche |
| 6,475,156 B1 | 11/2002 | Vega |
| 6,486,604 B1 | 11/2002 | Bradatsch |
| 6,487,274 B2 | 11/2002 | Bertsche |
| 6,501,981 B1 | 12/2002 | Schweikard et al. |
| 6,526,117 B1 | 2/2003 | Okerlund et al. |
| 6,526,156 B1 | 2/2003 | Black et al. |
| 6,661,617 B1 | 2/2003 | Hipwell, Jr. et al. |
| 6,527,443 B1 | 3/2003 | Vilsmeier et al. |
| 6,535,574 B1 | 3/2003 | Collins et al. |
| 6,546,124 B1 | 4/2003 | Hopple et al. |
| 6,569,092 B1 | 5/2003 | Guichon et al. |
| 6,611,617 B1 | 8/2003 | Crampton |
| 6,621,889 B1 | 9/2003 | Mostafavi |
| 6,635,021 B1 | 10/2003 | Sullivan et al. |
| 6,665,370 B2 | 12/2003 | Bruder et al. |
| 6,678,399 B2 | 1/2004 | Doi et al. |
| 6,690,965 B1 | 2/2004 | Riaziat et al. |
| 6,697,761 B2 | 2/2004 | Akatsuka et al. |
| 6,705,315 B2 | 3/2004 | Sullivan et al. |
| 6,724,930 B1 | 4/2004 | Kosaka et al. |
| 6,731,970 B2 | 5/2004 | Schlossbauer et al. |
| 6,766,064 B1 | 7/2004 | Langan et al. |
| 6,778,850 B1 | 8/2004 | Adler et al. |
| 6,888,919 B2 | 5/2005 | Graf |
| 6,904,126 B2 | 6/2005 | Endo |
| 6,937,696 B1 | 8/2005 | Mostafavi |
| 6,940,945 B2 | 9/2005 | Maschke |
| 6,980,679 B2 | 12/2005 | Jeung et al. |
| 6,984,208 B2 | 1/2006 | Zheng |
| 7,003,146 B2 | 2/2006 | Eck et al. |
| 7,006,862 B2 | 2/2006 | Kaufman et al. |
| 7,058,204 B2 | 6/2006 | Hildreth et al. |
| 7,062,078 B2 | 6/2006 | Weese et al. |
| 7,103,400 B2 | 9/2006 | Ossmann et al. |
| 7,123,758 B2 | 10/2006 | Jeung et al. |
| 7,158,610 B2 | 1/2007 | Mostafavi |
| 7,221,733 B1 | 5/2007 | Takai et al. |
| 7,227,925 B1 | 6/2007 | Mansfield et al. |
| 7,257,436 B2 | 8/2007 | Sasaki et al. |
| 7,260,426 B2 | 8/2007 | Schweikard et al. |
| 7,306,564 B2 | 12/2007 | Nakatani et al. |
| 7,314,451 B2 | 1/2008 | Halperin et al. |
| 7,349,522 B2 | 3/2008 | Yan et al. |
| 7,403,638 B2 | 7/2008 | Jeung et al. |
| 7,415,169 B2 | 8/2008 | Florent et al. |
| 7,609,810 B2 | 10/2009 | Yi et al. |
| 7,657,301 B2 | 2/2010 | Mate et al. |
| 7,657,302 B2 | 2/2010 | Mate et al. |
| 7,657,303 B2 | 2/2010 | Mate et al. |
| 7,769,430 B2 | 8/2010 | Mostafavi |
| 2001/0002934 A1 | 6/2001 | Oosawa |
| 2002/0023652 A1 | 2/2002 | Riaziat et al. |
| 2002/0091314 A1 | 7/2002 | Schlossbauer et al. |
| 2002/0097155 A1 | 7/2002 | Cassel et al. |
| 2002/0115931 A1 | 8/2002 | Strauss et al. |
| 2002/0118274 A1 | 8/2002 | Yahashi |
| 2002/0188194 A1 | 12/2002 | Cosman |
| 2002/0193685 A1 | 12/2002 | Mate et al. |
| 2003/0007593 A1 | 1/2003 | Heuscher et al. |
| 2003/0007601 A1 | 1/2003 | Jaffray et al. |
| 2003/0026758 A1 | 2/2003 | Baker |
| 2003/0063292 A1 | 4/2003 | Mostafavi |
| 2003/0072419 A1 | 4/2003 | Bruder et al. |
| 2003/0086596 A1 | 5/2003 | Hipp et al. |
| 2003/0099388 A1 | 5/2003 | Doi et al. |
| 2003/0135103 A1 | 7/2003 | Mistretta |
| 2003/0185450 A1 | 10/2003 | Garakani |
| 2003/0188757 A1 | 10/2003 | Yanof et al. |
| 2003/0210812 A1 | 11/2003 | Khamene et al. |
| 2004/0005088 A1* | 1/2004 | Jeung et al. ............... 382/128 |
| 2004/0068169 A1 | 4/2004 | Mansfield et al. |
| 2004/0071337 A1* | 4/2004 | Jeung et al. ............... 382/151 |
| 2004/0082853 A1 | 4/2004 | Takeshi et al. |
| 2004/0082874 A1 | 4/2004 | Aoki et al. |
| 2004/0092815 A1 | 5/2004 | Schweikard et al. |
| 2004/0092816 A1 | 5/2004 | Ossmann et al. |
| 2004/0097805 A1 | 5/2004 | Verard et al. |
| 2004/0114718 A1 | 6/2004 | Brown |

(56) References Cited

U.S. PATENT DOCUMENTS

| | | | |
|---|---|---|---|
| 2004/0116804 | A1 | 6/2004 | Mostafavi |
| 2004/0215077 | A1 | 10/2004 | Witt et al. |
| 2004/0218719 | A1 | 11/2004 | Brown et al. |
| 2004/0234115 | A1 | 11/2004 | Zijp et al. |
| 2004/0254773 | A1 | 12/2004 | Zhang et al. |
| 2004/0258307 | A1 | 12/2004 | Viola |
| 2005/0002546 | A1 | 1/2005 | Florent et al. |
| 2005/0027196 | A1 | 2/2005 | Fitzgerald |
| 2005/0053267 | A1 | 3/2005 | Mostafavi |
| 2005/0054916 | A1 | 3/2005 | Mostafavi |
| 2005/0080336 | A1 | 4/2005 | Byrd et al. |
| 2005/0113672 | A1 | 5/2005 | Salla et al. |
| 2005/0113711 | A1 | 5/2005 | Nakatani et al. |
| 2005/0201510 | A1 | 9/2005 | Mostafavi |
| 2005/0283068 | A1 | 12/2005 | Zuccolotto et al. |
| 2006/0165267 | A1 | 7/2006 | Wyman et al. |
| 2006/0241443 | A1 | 10/2006 | Whitmore et al. |
| 2007/0053491 | A1 | 3/2007 | Schildkraut et al. |
| 2007/0053494 | A1 | 3/2007 | Mostafavi |
| 2007/0189455 | A1 | 8/2007 | Allison |
| 2008/0144772 | A1 | 6/2008 | Yi et al. |

FOREIGN PATENT DOCUMENTS

| | | |
|---|---|---|
| EP | 0866607 A2 | 9/1998 |
| EP | 1050272 | 11/2000 |
| FI | 79458 | 9/1989 |
| JP | 58-136334 | 8/1983 |
| JP | 61-220628 | 9/1986 |
| JP | 4-364677 | 12/1992 |
| JP | 6-292085 | 10/1994 |
| JP | 7-275237 | 10/1995 |
| JP | 10-289321 | 10/1998 |
| JP | 2000262511 | 9/2000 |
| JP | 2000325339 | 11/2000 |
| JP | 2002090118 | 3/2002 |
| JP | 2002-533889 | 10/2002 |
| WO | 9816151 | 4/1998 |
| WO | 9830977 | 7/1998 |
| WO | 9838908 | 9/1998 |
| WO | 9852635 | 11/1998 |
| WO | 00/24466 | 5/2000 |
| WO | 0024333 | 5/2000 |
| WO | 02/26125 A2 | 4/2002 |
| WO | 00/77818 A1 | 10/2002 |
| WO | 02085455 | 10/2002 |
| WO | 03003796 | 1/2003 |

OTHER PUBLICATIONS

Ahlstrom, K.H. et al. "Pulmonary MR Angiography with Ultrasmall Superparamagnitic Iron Oxide Particles as a Blood Pool Agent and a Navigtor Echo for Respiratory Gating: Pilot Study" Radiology (Jun. 1999) 211(3):865-869.

Axel, L. et al. "Respiratory Effects in Two-Dimensional Fourier Transform MR Imaging" Radiology (Sep. 1986) 160 (3):795-801.

Balter, J.M. et al.; "Uncertainties in CT-Based Radiation Therapy Treatment Planning Associated With Patient Breathing"; Int. J. Radial. Oncol.. Bioi., Phys. 36; pp. 167-174 (Aug. 1996).

Bankman, I.N. et al. "Optimal Detection, Classification, and Superposition Resolution in Neural Waveform Recordings" IEEE ) Aug. 1993) 40(8):836-841).

Baroni, G. and G. Ferrigno "Real-time Motion Analysis for Definition and Control of Patient Position in Radiotherapy" SPIE 0-81942084-0/96 2709:506-515.

Bellenger, N.G. et al.; "Left Ventricular Quantification in Heart Failure by Cardiovascular MR Using Prospective OS Respiratory Navigator Gating: Comparison With Breath-Hold Acquisition"; J. Magn. Reson. Imaging 11; pp. 411-417; (Apr. 2000).

Cho, K. et al.; "Development of Respiratory Gated Myocardial SPECT System", J. Nucl. Cardial. 6; pp. 20-28; (Jan. IFeb. 1999).

Danias, P.G. et al. "Prospective Navigator Correction of Image Position for Coronary MR Angiography" Radiology (Jun. 1997) 203:733-736.

Davies, S.C. et al.; "Ultrasound Quantitation of Respiratory Organ Motion in the Upper Abdomen"; Br. J. Radiol. 67; pp. 1096-1102 (Nov. 1994).

Du, Y.P. "Prospective navigator gating with a dual acceptance window technique to reduce respiratory motion artifacts in 3D MR coronary angiography" Int'l J. Cardiovascular Imaging (2003) 19:157-162.

Du, Y.P. et al. "A comparison of prospective and retrospective respiratory navigator gating in 3D MR coronary angiography" Int'l J. Cardiovascular Imaging (2001) 17:287-294.

Ehman, R.L. et al.; "Magnetic Resonance Imaging With Respiratory Gating: Techniques and Advantages"; Am. J. Roenlgenol143; pp. 1175-1182 (Dec. 1984).

Fee, M.S. et al. "Automatic Sorting of Mulitple Unit Neuronal Signals in the Presence of Anisotropic and non-Gaussian Variability" J. Neuroscience Methods (1996) 69:175-188.

Felblinger, J. et al. "Effects of physiologic motion of the human brain upon quantitative H-MRS: analysis and correction by retrogating" NMR in Biomedicine (1998) 11:107-114.

Fishbein, K.W. et al. "The lever-coil: A simple, inexpensive sensor for respiratory and cardiac motion in MRI experiments" Magnetic Resonance Imaging (2001) 19:881-889.

Frolich, H.et al.;"A Simple Device for Breath-Level Monitoring During CT"; Radiology 156; p. 235 (Jul. 1985).

Gerig, L.H. et al. "The Development and Clinical Application of a Patient Position Monitoring System" Ottawa Regional Cancer Centre, General Division, 501 Smyth Rd., Ottawa, Ontario, Canada K1H8L6; National Research Council, IIT, Ottawa, Ontario, Canada K1A OR6; SpIE Videometrics III (1994) 2350:59-72.

Haacke, E.M. and G.W. Lenz "Improving MR Image Quality in the Presence of Motion by Using Rephasing Gradients" AJR (Jun. 1987) 148:1251-1258.

Hanley, J. et al.; "Deep Inspiration Breath-Hold Technique for Lung Tumors: The Potential Value of Target CS Immobilization and Reduced Lung Density in Dose Escalation"; Int. J. Radial. Oncol., Biol. Phys. 45; pp. 603-611 (Oct. 1999).

Henkelman, R.M. et al.; "How Important Is Breathing in Radiation Therapy of the Thorax?"; Int. J. Radiat. Onco/., Bioi., Phys. 8; pp. 2005-2010 (Nov. 1982).

Hofman, M.B.M. et al.; "MRI of Coronary Arteries: 20 Breath-Hold vs. 3D Respiratory-Gated Acquisition"; J. of Compo Assisted Tomography 19; pp. 56-62 (Jan.IFeb. 1995).

Huber, A. et al. "Navigator Echo-Based Respiratory Gating for Three-Dimensional MR Coronary Angiography: Results from Healthy Volunteers and Patients with Proximal Coronary Artery Stenoses" AJR (Jul. 1999) 173:95-101.

Iwasawa, Tae, et al.; "Normal In-Plane Respiratory Motion of the Bilateral Hemidiaphragms Evaluated by Sequentially Subtracted Fast Magnetic Resonance Images"; Journal of Thoracic Imaging; 1999; vol. 14, No. 2; pp. 130-134.

Johnson, L.S. et al.; "Initial Clinical Experience With a Video-Based Patient Positioning System"; Int. J. Radial. Oncol. Biol. Phys. 45; pp. 205-213; (Aug. 1999).

Jolesz, Ferenc M.D., et al.; "Image-Guided Procedures and the Operating Room of the Future"; Radiology; SPL Technical Report #48; May 1997: 204:601-612.

Josefsson, T. et al. "A Flexible High-Precision Video System for Digital Recording of Motor Acts Through Lightweight Reflex Markers" Computer Methods & Programs in Biomedicine (1996) 49:119-129.

Kachelriess, Marc, et al.; "Electrocardiogram-correlated Image Reconstruction From Subsecond Spiral Computed Tomography Scans of the Heart"; Med. Phys. 25(12); Dec. 1998; pp. 2417-2431.

Keatley, E. et al.; "Computer Automated Diaphragm Motion Quantification in a Fluoroscopic Movie"; Dept. of Medical Physics, Memorial Sloan-Kettering Cancer Center, New York; 3 pps. 1749-1751.

Kim, W.S., et al.; "Extension of Cardiac and Respiratory Motion Cycles by Use of Projection Data and Its Applications to NMR Imaging"; Magnetic Resonance in Medicine 13; 1990; pp. 25-37.

(56) References Cited

OTHER PUBLICATIONS

Korin, H.W. et al.; "Respiratory Kinematics of the Upper Abdominal Organs: A Quantitative Study"; Magn. Rason. Med. 23; pp. 172-178 (Jan. 1992).
Kubo, H.D. et al.; "Breathing-Synchronized Radiotherapy Program at the University of California Davis Cancer Center"; Med. Phys. 27(2); Feb. 2000; pp. 346-353.
Kubo, H.D. et al.; "Compatibility of Varian 2100C Gated Operations With Enhanced Dynamic Wedge and IMRT Dose Delivery"; Med. Phys. 27; pp. 1732-1738; (Aug. 2000).
Kubo, H.D. et al.; "Potential and Role of a Prototype Amorphous Silicon Array Electronic Portal Imaging Device in Breathing Synchronized Radiotherapy"; Med. Phys. 26(11); Nov. 1999; pp. 2410-2414.
Kubo, H.D. et al.; "Respiration Gated Radiotherapy Treatment: A Technical Study"; Phys. Mad. Bioi. 41; pp. 83-91; (1996).
Lee, M.W. and I. Cohen "Human Body Tracking with Auxiliary Measurements" IEEE International Workshop on Analysis and Modeling of Faces and Gestures (2003) 8 pages, located at htt/://iris.usc.edu/~icohen/projects/human/body/index.htm.
Lethimonnier, F. et al.; "Three-Dimensional. Coronary Artery MR Imaging Using Prospective Real-Time Respiratory DE Navigator and Linear Phase Shift Processing: Comparison With Conventional Coronary Angiography", Magn. Reson. Imaaine 17; DO. 1111-1120; (1999).
Lewis, C.E. et al.; "Comparison of Respiratory Triggering and Gating Techniques for the Removal of Respiratory Artifacts in MR Imaging"; Radiology 160; pp. 803-810; (Sep. 1986).
Li, D. et al.; "Coronary Arteries: Three-dimensional MR Imaging With Retrospective Respiratory Gating"; Radiology; Dec. 1996; vol. 201; No. 3.; pp. 857-863.
Lieberman, J.M. et al. Gated Magnetic Resonance Imaging of the Normal Diseased Heart: Radiology (Aug. 1984) 152:465-470.
Lopresti, B.J. et al. "Implementation and Performance of an Optical Motion Tracking System for High Resolution Brain PET Imaging" IEEE Transactions on Nuclear Science (Dec. 1999) 46(6):2059-2067.
Luker, Gary D., et al.; "Ghosting of Pulmonary Nodules With Respiratory Motion: Comparison of Helical and ConvenHonal CT Using an In Vitro Pediatric Model"; AJR:167; Nov. 1996; pp. 1189-1193.
Mageras, G. et al.; "Initial Clinical Evaluation of a Respiratory Gating Radiotherapy System"; 22nd Annual EMBS International Conference, Chicago. IL.; pp. 2124-2127; (Jul. 23-28, 2000).
Mageras, G.S. et al.; "Respiratory Motion-Induced Treatment Uncertainties"; Patras Medical Physics 99—VI International Conference on Medical Physics, Monduzzi Editore; pp. 33-39; (Sep. 1999).
Mageras, G.S., "Interventional Strategies for Reducing Respiratory-Induced Motion in External Beam Therapy"; The Use of Computers in Radiation Therapy XIIIth International Conference, Heidelberg, Germany; pp. 514-516; (May 2000).
Mah, D. et al.; "Technical Aspects of the Deep Inspiration Breath Hold Technique in the Treatment of Thoracic Cancer"; Int. J. Radiat. Oncol., Bioi., Phys. 48; pp. 1175-1185; (Nov. 2000).
Mah, K. et al.; "Time Varying Dose Due to Respiratory Motion During Radiation Therapy of the Thorax"; Proceedings of the Eighth Int'l Conference on the Use of Computers in Radiation Therapy, Toronto, Canada; Jul. 9-12, 1984; 00. 294-298.
Malone, S. et al.; "Respiratory-Induced Prostate Motion: Quantification and Characterization", Int. J. Radial. Oneal., Bioi., Phys. 48; pp. 105-109; (Aug. 2000).
Manke, D. et al. "Model Evaluation and Calibration for Prospective Respiratory Motion Correction in Coronary MR Angiography Based on 3-D Image Registration" IEEE Transactions on Medical Imaging (Sep. 2002) 21(9):1132-1141.
Manke, D. et al. "Respiratory Motion in Coronary Magnetic Resonance Angiography: A Comparison of Different Motion Models" J. Magnetic Resonance Imaging (2002) 15:661-671.
Final Office Action dated May 20, 2010 for U.S. Appl. No. 10/655,920.
Non Final Office Action dated Jul. 7, 2010 for U.S. Appl. No. 10/678,741.
Final Office Action dated Aug. 5, 2010 for U.S. Appl. No. 10/656,478.
McConnell, M.V. et al. "Comparison of Respiratory Suppression Methods and Navigator Locations for MR Coronary Angiography" AJR (May 1997) 168:1369-1375.
McConnell, M.V. et al. "Prospective Adaptive Navigator Correction for Breath-Hold MR Coronary Angiography" MRM (1997) 37:148-152.
Moerland, M.A. et al.; "The Influence of Respiration Induced Motion of the Kidneys on the Accuracy of CZ Radiotherapy Treatment Planning, A Magnetic Resonance Imaging Study", Radiotherapy Oncol. 30, pp. 150-154 (1994).
Mori, M. et al.; "Accurate Contiguous Sections Without Breath-Holding on Chest CT; Value of Respiratory Gating and Ultrafast CT"; AJR:162. May 1994; pp. 1057-1062.
Mostafavi, H.; "Method and System for Radiation Application"; U.S. Appl. No. 10/678,741, filed Oct. 3, 2003; Specification 63 pgs.; Claims 9 pgs; Abstract 1 pg; Drawings 22 pgs.
Mostafavi, Hassan; "Overview of Post-Processing Algorithm to Create Volumetric Motion Sequences"; Varian Medical Systems, Inc.; May 2, 2002; 1 page.
Nevatia, R. et. Al. "Human Body Tracking with Articulated Human Body Model" (Nov. 2002) pp. 1-3.
Nikolaou, K. et al. "Navigator Echo-Based Respiratory Gating for Three-Dimensional MR Coronary Angiography: Reduction of Scan Time Using a Slice Interpolation Technique" J. Computer Assisted Tomography (2001) 25 (3):378-387.
Ohara, K. et al.; "Irradiation Synchronized With Respiration Gate"; Int. J. Radial. Oncol., Biol. Phys. 17; pp. 853- 857; (Oct. 1989).
Oshinski, J.N. et al.; "Two-Dimensional Coronary MR Angiography Without Breath Holding"; Radiology 201; pp. 737-743; (Dec. 1996).
Paradis, A.L. et al. "Detection of Periodic Signals in Brain Echo-Planar Functional Images" IEEE (Jan. 1, 1997) pp. 696-697.
Peltola, Seppo M.Sc.; "Gated Radiotherapy to Compensate for Patient Breathing"; Proceedings of the Eleventh Varian Users Meeting; Macro Island, Florida; May 11-13, 1986; 4 pages.
Plein, S. et al. "Three-Dimensional Coronary MR Angiography Performed with Subject-Specific Cardiac Acquisition Windows and Motion-Adapted Respiratory Gating" AJR (Feb. 2003) 180:505-512.
Post, J.C. et al. "Three-Dimensional Respiratory-Gated MR Angiography of Coronary Arteries: Comparison with Conventional Coronary Angiography" AJR (Jun. 1996) 166:1399-1404.
Ramsey, C.R. et al.; "Clinical Efficacy of Respiratory Gated Conformal Radiation Therapy", Medical Dosimetry 24; pp. 115-119: (1999).
Ramsey, C.R. et al.;"A Comparison of Beam Characteristics for Gated and Nongated Clinical X-Ray Beams"; Med. Phys. 26; pp. 2086-2091; (Oct. 1999).
Regenfus, M. et al. "Comparison of Contrast-Enhanced Breath-Hold and Free-Breathing Respiratory-Gated Imaging in Three-dimensional Magnetic Resonance Coronary Angiography" Am. J. Cardiology (Oct. 1, 2002) 90:725-730.
Ritchie, C. J., et al.; "Predictive Respiratory Gating: A New Method to Reduce Motion Artifacts on CT Scans"; Radiology; 1994; pp. 847-852; vol. 190; No. 3.
Robinson, Terry E., et al.; "Standardized High-Resolution CT of the Lung Using a Spirometer-Triggered Electron Beam CT Scanner"; AJR:172; Jun. 1999; pp. 1636-1638.
Rogus, R.D. et al.; "Accuracy of a Photogrammetry-Based Patient Positioning and Monitoring System for Radiation Therapy"; Med. Phys. 26; pp. 721-728; (May 1999).
Rosenzweig, K.E. et al.; The Deep Inspiration Breath Hold Technique in the Treatment of Inoperable Non-Small-Cell Lung Cancer; Inl. J. Radiat. Oncol., Biol.. Phys. 48; pp. 81-87; (Aug. 2000).
Ross, C.S. et al.; "Analysis of Movement of Intrathoracic Neoplasms Using Ultrafast Computerized Tomography"; Int. J. Radia/. Oncol., Bioi., Phys. 18; pp. 671-677; (Mar. 1990).
Runge, V.M. et al.; "Respiratory Gating in Magnetic Resonance Imaging at 0.5 Tesla"; Radiology 151; pp. 521-523; (May 1984).

(56) References Cited

OTHER PUBLICATIONS

Sachs, T.S. et al.; "Real-Time Motion Detection in Spiral MRI Using Navigators", Magn. Reson. Med. 32; pp. 639-645; (Nov. 1994).
Schar, M. et al. "The Impact of Spatial Resolution and Respiratory Motion on MR Imaging of Atherosclerotic Plaque" J. Magnetic Resonance Imaging (2003) 17:538-544.
Schwartz, L.H. et al.; "Kidney Mobility During Respiration"; Radio/her. Oncol. 32; pp. 84-86; (1994).
Shirato, H. et al.; "Four-Dimensional Treatment Planning and Fluroscopic Real-Time Tumor Tracking Radiotherapy for Moving Rumor"; Int. J. Radial. Oncol., Bioi., Phys. 48; pp. 435-442; (Sep. 2000).
Sinkus, Ralph. et al.; "Motion Pattern Adapted Real-Time Respiratory Gating"; Magnetic Resonance in Medicine 41; 1999; pp. 148-155.
Solberg, Timothy D., et al.; "Feasibility of Gated IMRT"; Proceedings of the 22nd Annual International Conference of the IEEE Engineering in Medicine and Biology Society, Chicago, IL (Jul. 23-28, 2000) 3pps: 2732-2734.
Spuentrup, E. et al. "Respiratory motion artifact suppression in diffusion-weighted MR imaging of the spine" Eur. Radiol. (2003) 13:330-336.
Suramo, M.P. et al.; "Cranio-caudal Movements of the Liver, Pancreas and Kidneys on Respiration", Acta Radiol. Diagn. 2; pp. 129-131; (1984).
Tada, Takuhito, et al.; "Lung Cancer: Intermittent Irradiation Synchronized With Respiratory Motion—Results of a Pilot Study"; Radiology, Jun. 1998; vol. 207; No. 3; pp. 779-783.
Thickman, D. et al. "Phase-Encoding Direction upon Magnetic Resonance Image Quality of the Heart" Magnetic Resonance in Medicine (1988) 6:390-396.
Van Geuns, R.J.M. et al.; "Magnetic Resonance Imaging of the Coronary Arteries: Clinical Results From ThreeDimensional Evaluation of a Respiratory Gated Technique"; Heart 82; pp. 515-519; (Oct. 1999).
Wang, Y. et al. "Navigator-Echo-based Real-Time Respiratory Gating and Triggering for Reduction of Respiration Effects in Three-dimensional Crornary MR Angiography" Radiology (1996) 198:55-60.
Wang, Y. et al. "Respiratory Motion of the Heart: Kinematics and the Implication for the Spatial Resolution in Coronary Imaging" Magnetic Resonance in Medicine (1995) 33:713-719.
Wang, Y. et al.; "Implications for the Spatial Resolution in Coronary Imaging"; Magnetic Resonance in Medicine 33; 1995; pp. 713-719.
Weber, C. et al. "Correlation of 3D MR coronary angiography with selective coronary angiography: feasibilitly of the motion adapted gating technique" Eur. Radiol. (2002) 12:718-726.
Weiger, Markus, et al.; "Motion-Adapted Gating Based on k-Space Weighting for Reduction of Respiratory Motion Artifacts"; Magnetic Resonance in Medicine 38; 1997; pp. 322-333.
Wiesmann, F. "High-Resoulution MRI with Cardiac and Respiratory Gating Allows for Accurate in Vivo Atherosclerotic Plaque Visualization in the Muring Aortic Arch" Magnetic Resonance in Medicine (2003) 50:69-74.
Wong, J.W. et al.; "The Use of Active Breathing Control (ABC) to Reduce Margin for Breathing Motion"; In/. J. Radial. Oncol., Phys. 44; pp. 911-919; (Jul. 1999).
Wood, M. L. and R. M. Henkelman "Suppression of respiratory motion artifacts in magnetic resonance imaging" Med. Phys. (Nov./Dec. 1996) 13(6):794-805.
Woodard, P.K., et al.; "Detection of Coronary Stenoses on Source and Projection Images Using Three-Dimensional MR Angiography With Retrospective Respiratory Gating: Preliminary Experience"; AJR:170; Apr. 1998; No. 4; 00. 883-888.
Worthley, S.G. et al. "Cardiac gated breath-hold back blood MRI of the coronary artery wall: An in vivo and ex-vivo comparison" Int'l J. Cardiovascular Imaging (2001) 17:195-201.
Yamashita, Y. et al. "MR Imaging of Focal Lung Lesions: Elimination of Flow and Motion Artifact by Breath-Hold ECG-Gated and Black-Blood Techniques on T2-Weighted Turbo SE and STIR Swquences" J. Magnetic Resonance Imaging (1999) 9:691-698.
Yorke, E. et al.; "Respiratory Gating of Sliding Window IMRT"; 22nd Annual EMBS International Conference. Chicago, IL.; pp. 2118-2121; (Jul. 23-28, 2000).
Kutcher, G.J. et al.; "Control; Correction, and Modeling of Setup Errors and Organ Motion", Semin. Radiat. Oncol. 5; pp. 134-145 (Apr. 1995).
Yuan, Q. et al.; "Cardiac-Respiratory Gating Method for Magnetic Resonance Imaging of the Heart"; Magn. Reson. Med. 43; pp. 314-318; (Feb. 2000).
Vedam, S.S. et al., "Acquiring a four-dimensional computed tomography dataset using an external respiratory signal" Phys. Med. Bio. 48 (2003), pp. 45-62.
International Search Report and Written Opinion dated Feb. 5, 2007 for PCT/US2005/034999.
Non Final Office Action dated Mar. 4, 2010 for U.S. Appl. No. 11/116,699.
Final Office Action dated Feb. 28, 2011 for U.S. Appl. No. 11/116,699.
Adler Jr. et al., "Image-Guided Robotic Radiosurgery". Neurosurgery, vol. 44, No. 6, Jun. 1999.
Murphy et al., "Patterns of Patient Movement During Frameless Image-Guided Radiosurgery". International Journal of Radiation Oncology Biology Physics, vol. 55, No. 5, Apr. 1, 2003.
Neicu et al., "Synchronized Moving Aperture Radiation Therapy (SMART): Average Tumour Trajectory for Lung Patients". Physics in Medicine and Biology, vol. 48, No. 5, Mar. 7, 2003.
European Supplementary Search Report for EP Application No. 04783114.4 dated Dec. 30, 2010.
Non-Final Office Action dated Nov. 9, 2010 for U.S. Appl. No. 10/655,920.
Final Office Action dated Dec. 8, 2010 for U.S. Appl. No. 10/678,741.
Non-Final Office Action dated Sep. 14, 2010 for U.S. Appl. No. 11/116,699.
International Search Report and Written Opinion dated Dec. 1, 2005 (PCT/US05/08037).
International Search Report and Written Opinion dated Oct. 13, 2005 (PCT/US04/32381).
International Search Report, Varian Medical Systems, Inc. PCT/US03/27552, dated Feb. 19, 2004.
Preliminary Search Brochure entitled "Kinematic Measurement Systems" by Qualisys printed Apr. 4, 1994; 4 pages.
International Search Report for PCT/US03/36454 dated May 28, 2004.
International Search Report and Written Opinion dated Feb. 15, 2005 for PCT/US2004/029277.
International Search Report and Written Opinion dated Jan. 30, 2006 for PCT/US2004/028571.
International Search Report and Written Opinion dated Mar. 15, 2005 for PCT/US2004/028756.
Non Final Office Action dated Aug. 4, 2009 for U.S. Appl. No. 10/678,741.
Non Final Office Action dated Aug. 19, 2008 for U.S. Appl. No. 10/678,741.
Non Final Office Action dated Jan. 16, 2008 for U.S. Appl. No. 10/678,741.
Final Office Action dated Feb. 17, 2009 for U.S. Appl. No. 10/678,741.
Non Final Office Action dated Aug. 21, 2009 for U.S. Appl. No. 11/116,699.
Non Final Office Action dated Apr. 3, 2009 for U.S. Appl. No. 12/182,932.
Final Office Action dated Nov. 3, 2009 for U.S. Appl. No. 12/182,932.
Non Final Office Action dated Nov. 2, 2009 for U.S. Appl. No. 10/655,920.
Non Final Office Action dated Oct. 28, 2008 for U.S. Appl. No. 10/655,920.
Non Final Office Action dated Oct. 18, 2007 for U.S. Appl. No. 10/655,920.
Non Final Office Action dated Jan. 30, 2007 for U.S. Appl. No. 10/655,920.
Final Office Action dated May 8, 2009 for U.S. Appl. No. 10/655,920.
Final Office Action dated Apr. 29, 2008 for U.S. Appl. No. 10/655,920.

(56) References Cited

OTHER PUBLICATIONS

Non Final Office Action dated Nov. 21, 2008 for U.S. Appl. No. 10/656,478.
Non Final Office Action dated May 20, 2008 for U.S. Appl. No. 10/656,478.
Non Final Office Action dated Jun. 13, 2007 for U.S. Appl. No. 10/656,478.
Non Final Office Action dated Dec. 13, 2006 for U.S. Appl. No. 10/656,478.
Non Final Office Action dated Jan. 26, 2010 for U.S. Appl. No. 10/656,478.
Final Office Action dated May 5, 2009 for U.S. Appl. No. 10/656,478.
Final Office Action dated Nov. 5, 2007 for U.S. Appl. No. 10/656,478.
Final Office Action dated Jan. 27, 2012 for U.S. Appl. No. 10/678,741
Advisory Action dated Apr. 20, 2012 for U.S. Appl. No. 10/678,741.
Japanese Notice of Reasons for Refusal dated Jan. 5, 2012 for JP Application No. 2006-525439.
Japanese Notice of Reasons for Refusal dated Jul. 25, 2011 for JP Application No. 2006-525439.
Japanese Notice of Reasons for Refusal dated Aug. 9, 2010 for JP Application No. 2006-525439.
European Office Action dated Mar. 12, 2012 for EP Application 04782961.9.
European Office Action dated Apr. 21, 2010 for EP Application 04782961.9.
European Office Action dated Mar. 29, 2011 for EP Application 04782961.9.
European Office Action dated Sep. 7, 2010 for EP Application 04782961.9.
European Office Action dated Apr. 28, 2011 for EP Application 04783114.4.
Japanese Decision to Dismiss the Amendment dated Aug. 31, 2011 for JP Application 2006-526196.
Japanese Notice of Reason for Refusal dated Feb. 21, 2011 for JP Application 2006-526196.
Japanese Notice of Reason for Refusal dated Aug. 3, 2010 for JP Application 2006-526196.
Japanese Notice of Reason for Refusal dated Apr. 7, 2010 for JP Application 2006-526196.
European Office Action dated Aug. 21, 2009 for EP Application 04793980.6.
European Office Action dated Mar. 8, 2011 for EP Application 04793980.6.
European Office Action dated Oct. 7, 2010 for EP Application 04783505.3.
European Supplementary Search Report dated Jun. 16, 2010 for EP Application 04783505.3.
Japanese Notice of Reason for Refusal dated Oct. 6, 2009 for JP Application 2006-525540.
Japanese Notice of Reason for Refusal dated Mar. 17, 2010 for JP Application 2006-525540.
Japanese Notice of Reason for Refusal dated Mar. 22, 2011 for JP Application 2006-525540.
Japanese Decision of Refusal dated Apr. 21, 2009 for JP Application 2003-509826.
Notice of Questioning for Shimpan Appeal dated Apr. 26, 2010 for JP Application 2003-509826.
Non-Final Office Action dated Apr. 17, 2012 for U.S. Appl. No. 12/205,431.
European Supplementary Search Report for EP Application No. 04793980.6 dated Mar. 12, 2009.
Non Final Office Action dated Jun. 11, 2012 for U.S. Appl. No. 10/655,920.
Bifulco P et al., "Automatic Recognition of Vertebral Landmarks in Fluoroscopic Sequences for Analysis of Intervertebral Kinematics", Medical and Biological Engineering and Computing, Springer, Heildelberg, DE, vol. 39, No. 1, Jan. 1, 2011, 12 pages.
Eisner R L et al., "Use of Cross-Correlation Function to Detect Patient Motion During Spect Imaging", Journal of Nuclear Medicine, Society of Nuclear Medicine, Reston, VA, US, vol. 28, No. 1, Jan. 1, 1987, 6 pages.
European Office Action dated Jun. 14, 2012 for EP Application No. 04793980.6.
European Search Report and Opinion dated May 24, 2012 for EP Application No. 12164387.8.
European Office Action dated Jun. 5, 2012 for EP Application No. 04783114.4.
Final Office Action dated Apr. 26, 2011 for U.S. Appl. No. 10/655,920.
Non-Final Office Action dated Aug. 12, 2011 for U.S. Appl. No. 12/182,932.
Non-Final Office Action dated Jul. 20, 2011 for U.S. Appl. No. 10/678,741.
Final Office Action dated Dec. 16, 2011 for U.S. Appl. No. 12/182,932.
Japanese Notice of Questioning for Shimpan Appeal dated Sep. 12, 2012, for JP Application No. 2006-526196.
English Translation of Japanese Notice of Questioning for Shimpan Appeal dated Sep. 12, 2012, for JP Application No. 2006-526196.
English Abstract for Application No. JP 6-292085 dated Oct. 18, 1994.
English Abstract for Application No. JP 7-275237 dated Oct. 24, 1995.
English Abstract for Application No. JP 10-289321 dated Oct. 27, 1998.
Final Office Action dated Oct. 11, 2012, for U.S. Appl. No. 12/205,431.
Notice of Reasons for Refusal dated Dec. 17, 2012 for Japanese Patent Application No. 2011-25872.
Office Action dated Nov. 7, 2012 for European Patent Application No. 04783114.4.
Final Office Action dated Feb. 1, 2013 for U.S. Appl. No. 10/655,920.
Advisory Action dated Jan. 9, 2013 for U.S. Appl. No. 12/205,431.
Advisory Action dated Apr. 10, 2013 for U.S. Appl. No. 10/655,920.
Notice of Reasons for Refusal dated Feb. 12, 2013 for JP Patent Application No. 2006-526196.
English Translation of Notice of Reasons for Refusal dated Feb. 12, 2013 for JP Patent Application No. 2006-526196.
First Examination Report dated Feb. 21, 2013 for EP Patent Application No. 12 164 387.8.
Final Office Action dated Nov. 7, 2012, for U.S. Appl. No. 12/182,932.
Final Office Action dated Dec. 19, 2012, for U.S. Appl. No. 10/656,478.
Office Action dated Aug. 2, 2013 for EP Patent Application No. 04793980.6, 4 pages.
E.C. Ford et al., "Respiration-correlated spiral CT: A method of measuring respiratory-induced anatomic motion for radiation treatment planning" Med. Phys. 30 (1), Jun. 13, 2002, 12 pages.
Final Office Action dated May 1, 2015 for U.S. Appl. No. 11/116,699.
Non-final Office Action dated Jul. 15, 2015 for U.S. Appl. No. 14/246,705.
Non-final Office Action dated May 31, 2013 for U.S. Appl. No. 10/678,741.
Notice of Allowance and Fees Due dated Jun. 19, 2013 for U.S. Appl. No. 10/655,920.
Final Office Action dated Jan. 13, 2016 for related U.S. Appl. No. 14/246,705.
Advisory Action dated Mar. 30, 2016 for related U.S. Appl. No. 14/246,705.
Intention to Grant dated Jan. 27, 2014 for related EP Patent Application No. 04793980.6.
Non-final Office Action dated Aug. 22, 2016 for related U.S. Appl. No. 14/246,705.
European Communication dated Nov. 14, 2013 for related EP Patent Application No. 04793980.6.
Non-final Office Action dated May 3, 2016 for related U.S. Appl. No. 10/656,478.
Notice of Reasons for Refusal dated Apr. 10, 2013, for JP Patent Application No. 2011-025872.
English Translation of Notice of Reasons for Refusal dated Apr. 10, 2013 for JP Patent Application No. 2011-025872.

(56) References Cited

OTHER PUBLICATIONS

Non-final Office Action dated Sep. 6, 2016 for related U.S. Appl. No. 12/182,932.
Non-final Office Action dated Oct. 4, 2016 for related U.S. Appl. No. 12/205,431.
Notice of Allowance and Fee(s) due dated Aug. 31, 2015 for related U.S. Appl. No. 11/116,699.
Non-final Office Action dated Sep. 29, 2014 for U.S. Appl. No. 11/116,699.
Non-final Office Action dated Jul. 7, 2017 for related U.S. Appl. No. 10/656,478.
Non-final Office Action dated Jul. 21, 2017 for related U.S. Appl. No. 12/205,431.
Advisory Action dated Aug. 8, 2017 for related U.S. Appl. No. 14/246,705.
Non-final Office Action dated Sep. 18, 2017 for related U.S. Appl. No. 12/182,932.
Final Office Action dated Jan. 20, 2017 for related U.S. Appl. No. 10/656,478.
Final Office Action dated Mar. 7, 2017 for related U.S. Appl. No. 12/205,431.
Final Office Action dated Apr. 3, 2017 for related U.S. Appl. No. 12/182,932.
Advisory Action dated May 9, 2017 for related U.S. Appl. No. 10/656,478.
Final Office Action dated May 9, 2017 for related U.S. Appl. No. 14/246,705.
Advisory Action dated May 17, 2017 for related U.S. Appl. No. 12/205,431.
Non-final Office Action dated Oct. 31, 2017 for related U.S. Appl. No. 14/246,705.
Final Office Action dated Jan. 9, 2018 for related U.S. Appl. No. 12/205,431.
Final Office Action dated Jan. 22, 2018 for related U.S. Appl. No. 10/656,478.
Final Office Action dated Feb. 26, 2018 for related U.S. Appl. No. 12/182,932.
Advisory Action dated Apr. 19, 2018 for related U.S. Appl. No. 12/205,431.
Advisory Action dated Apr. 12, 2018 for related U.S. Appl. No. 10/656,478.
Final Office Action dated Jul. 13, 2018 for related U.S. Appl. No. 14/246,705.
Non-Final Office Action dated Sep. 26, 2018 for related U.S. Appl. No. 12/182,932, 7 pages.
Advisory Action dated Oct. 5, 2018 for related U.S. Appl. No. 14/246,705, 3 pages.
Notice of Allowance and Fees Due dated Oct. 15, 2013 for U.S. Appl. No. 10/678,741.
Non-Final Office Action dated Apr. 24, 2019 for related U.S. Appl. No. 14/246,705, 16 pages.
Final Office Action dated May 10, 2019 for related U.S. Appl. No. 12/182,932, 7 pages.
Final Office Action dated Sep. 27, 2019 for related U.S. Appl. No. 14/246,705.
Advisory Action dated Aug. 23, 2019 for related U.S. Appl. No. 12/182,932.
Notice of Allowance dated Jan. 2, 2020 for related U.S. Appl. No. 14/246,705.

\* cited by examiner

SYSTEMS AND METHODS FOR DETERMINING A STATE OF A PATIENT

RELATED APPLICATION DATA

The application is related to U.S. patent application Ser. No. 12/205,431, filed on Sep. 5, 2008.

FIELD

The present application relates to medical methods and systems, and more particularly, to methods and systems for monitoring activity of a patient, such as a breathing activity of an infant.

BACKGROUND

A serious concern for parents of a newborn is the possibility of death by Sudden Infant Death Syndrome (SIDS). SIDS is commonly known as the sudden death of an infant under one year of age which remains unexplained after a thorough case investigation, including performance of a complete autopsy, examination of the death scene, and review of the clinical history. A SIDS death occurs quickly and is often associated with sleep, with no signs of suffering.

Although exact causes of SIDS are still unknown, mounting evidence suggests that some SIDS babies are born with brain abnormalities that make them vulnerable to sudden death during infancy. Studies of SIDS victims reveal that some SIDS infants have abnormalities in the "arcuate nucleus," a portion of the brain that is likely to be involved in controlling breathing during sleep. However, scientists believe that the abnormalities that are present at birth may not be sufficient to cause death. Other factors, such as lack of oxygen and excessive carbon dioxide intake, may also contribute to the occurrence of SIDS. During sleep, a baby can experience a lack of oxygen and excessive carbon dioxide levels when they re-inhale the exhaled air. Normally, an infant can sense such inadequate air intake, and his breathing movement can change accordingly to compensate for the insufficient oxygen and excess carbon dioxide. As such, certain types of irregularity in an infant's breathing activity can be an indicator of SIDS or the likelihood of SIDS.

Therefore, monitoring of an infant's breathing activity for breathing irregularities could help prevent or detect the possibility of SIDS. One approach to monitor the breathing activity is to attach to the body of the infant a battery-powered electronic device that can mechanically detect the breathing movement. Although such device can monitor the infant's breathing directly, the battery can render the device large and heavy, which encumbers the tiny infant. Additionally, difficulty of attachment can be expected under this approach.

Another approach to monitor an infant's breathing activity is to install a pressure sensitive pad underneath the mattress where the infant is sleeping. The pad monitors the baby's breathing activity by measuring body movement. However, because the pad is unable to directly monitor the breathing movement, accuracy of the generated breathing data can be affected.

In another approach, a marker block with a plurality of markers is coupled to the infant's chest. By continuously tracking the positions of the markers, an infant's breathing movement can then be monitored during sleep.

SUMMARY

In accordance with some embodiments, a method of monitoring a patient includes obtaining a first image of an object, obtaining a second image of the object, determining a level of similarity between the first and second images, obtaining a third image of the object, determining a level of similarity between the first and third images, analyzing a time series of values that includes the determined level of similarity between the first and second images and the determined level of similarity between the first and third images, and determining a state of the patient based at least on a result of the act of analyzing.

In accordance with other embodiments, a computer product having a set of instruction, an execution of which causes a process to be performed, the process includes obtaining a first image of an object, obtaining a second image of the object, determining a level of similarity between the first and second images, obtaining a third image of the object, determining a level of similarity between the first and third images, analyzing a time series of values that includes the determined level of similarity between the first and second images and the determined level of similarity between the first and third images, and determining a state of the patient based at least on a result of the act of analyzing.

In accordance with some embodiments, a system for monitoring a patient includes means for obtaining a first image of an object, a second image of the object, and a third image of the object, means for determining a level of similarity between the first and second images, and a level of similarity between the first and third images, means for analyzing a time series of values that includes the determined level of similarity between the first and second images and the determined level of similarity between the first and third images, and means for determining a state of the patient based at least on a result of the act of analyzing.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
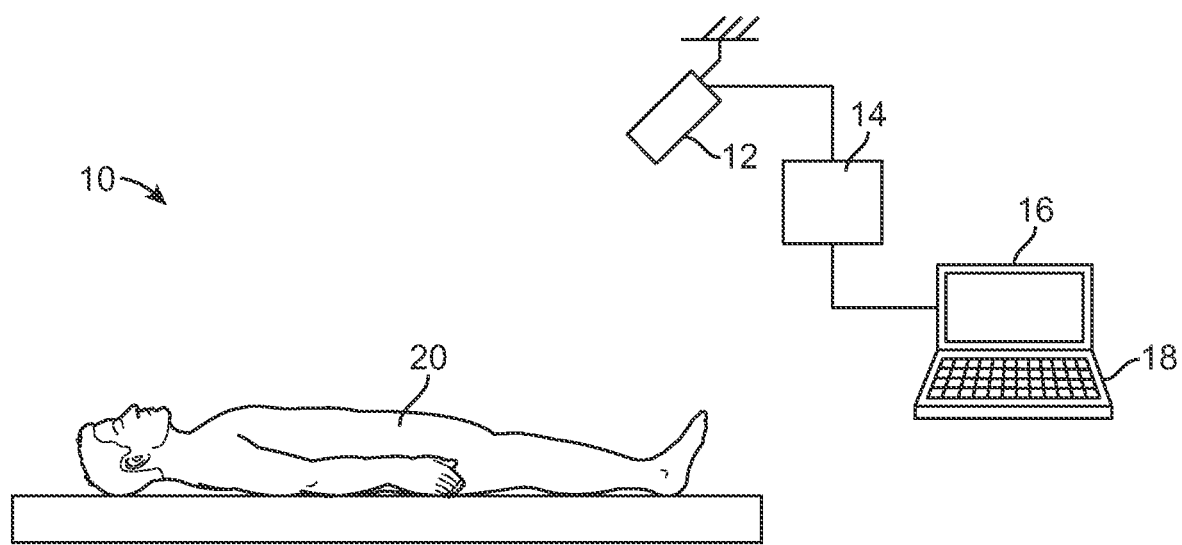
FIG. 1 is a block diagram of a patient monitoring system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a patient monitoring system 10 in accordance with some embodiments. The patient monitoring system 10 includes an optical device 12, and a processor 14. The optical device may be, for example, a charge-coupled device, such as a camera. In some embodiments, the camera may have an auto-focusing feature that allows the camera to automatically focus on a portion of an object that it is viewing. Alternatively, the optical device may be another type of imaging device that is capable of obtaining images of a patient. In the illustrated embodiments, the processor 14 is illustrated as a separate device from the optical device 12. In other embodiments, the processor 14 may be incorporated internally within the optical device 12, in which case, the processor 14 becomes a part of the optical device 12. In some embodiments, the system 10 may further includes a monitor 16 and a user interface 18, such as a keyboard and/or a mouse. In other embodiments, the user interface 18 may include one or more buttons that are integrated with the optical device 12. In such cases, the optical device 12 may also includes a screen, such as a LCD screen for displaying information.

During use, the optical device 12 is placed or mounted onto a structure, such as a table, a ceiling, or a patient support, and the optical device 12 is used to view a patient 20. The processor 14 receives images from the optical device 12, processes the images, and determine information regarding the patient 20. If the system 10 includes the monitor 16, images generated by the optical device 12 and information determined by the processor 14 may be displayed in the monitor 16.

Figure 2:
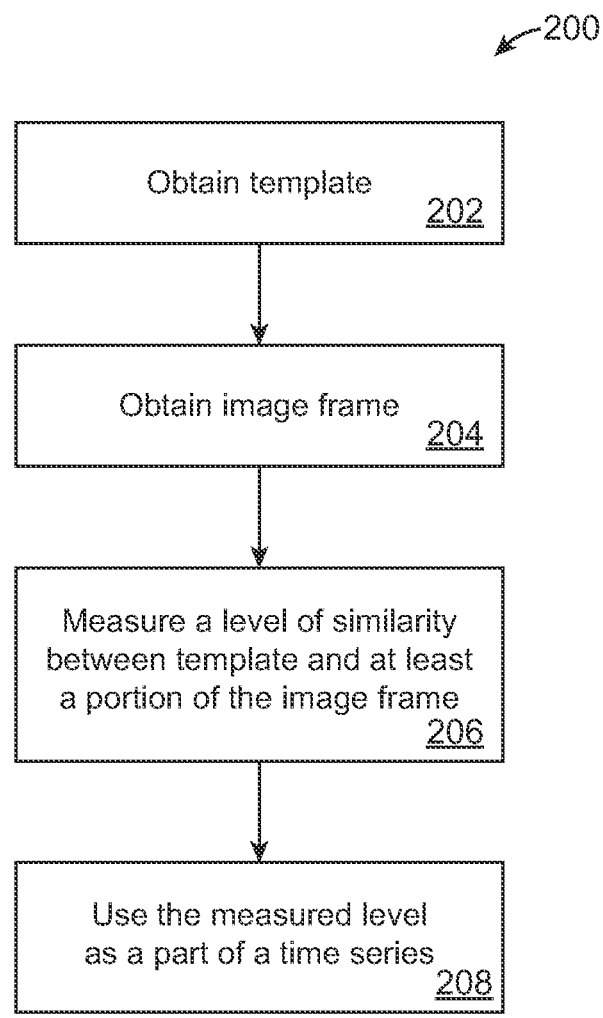
FIG. 2 illustrates a method of using the system of FIG. 1 in accordance with some embodiments.

FIG. 2 illustrates a method 200 of using the system 10 in accordance with some embodiments. To set up for the method 200, the optical device 12 is mounted in a fixed position and orientation such that its field of view includes at least a portion of an object that moves due to the patient's breathing. For example, the optical device 12 can be pointed at the blanket covering a sleeping infant, or the clothing or skin of the patient 20 lying on a couch of an imaging or radiation treatment machine. Depending on the application, the coverage area of the moving object can range from a few to more than one thousand square centimeters. In some cases, if the optical device 12 is a camera, the focal length of the camera lens may be selected such that a desired coverage area is achieved for the camera distance that is convenient for a particular application and installation.

Figure 3:
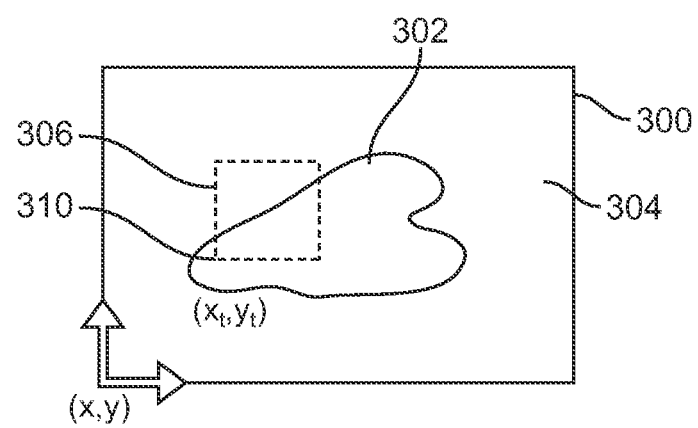
FIG. 3 illustrates an example of a template in accordance with some embodiments.

To begin method 200, an image template is obtained (step 202). In the illustrated embodiments, the optical device 12 is aimed at the object that moves with breathing to view at least a portion of such object, and an image frame is generated by the optical device 12. The object may be a part of the patient, or any object that is coupled with the patient, such as clothes (or portion thereof), blanket (or portion thereof), marker, etc. A portion of the image frame is then selected as the image template. In the illustrated embodiments, an area within the image frame over which there is some object movement is selected as the template. FIG. 3 illustrates an example of an image frame 300 that includes an image 302 of an object and an image 304 of a background. In the example, as the patient 20 undergoes breathing motion, the area 306 in the image frame 300 and other image frames in a sequence capture images of a part of the object that moves with breathing. Thus, the area 306 of the image frame 300 is selected as the image template in the example. In the illustrated embodiments, the position $(X_t, Y_t)$ 310 of the area 306 relative to the image frame 300 coordinate (X, Y) is stored for later use. Various techniques for obtaining the image template will be further described below. In some embodiments, an area in the image frame in which the patient's movement is the greatest may be selected for use as the image template. In other embodiments, instead of using an area in the image frame in which the patient's movement is the greatest, any area in the image frame in which there is some patient's movement (which may not be the greatest movement) may be used. Also, in other embodiments, instead of selecting a portion of the image frame as the image template, the entire image frame may be used as the image template. In some cases, if an image does not include any object that moves (e.g., an object that moves with breathing), the processor is configured to detect such condition, and generate an alert so that a user can adjust the camera, e.g., by aiming it towards a different direction.

Figure 4:
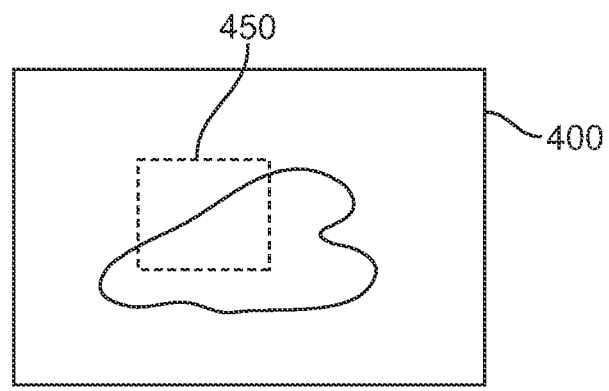
FIG. 4 illustrates examples of image frames in accordance with some embodiments.

Next, the optical device 12 is continued to view the object moving with breathing, and provides another image frame (input image) that contains an image of at least a portion of the patient 20 (step 204). FIG. 4 illustrates an example of another image frame 400. The image frame 400 contains an image of at least a part of the patient 20 that is captured when the patient 20 is breathing. Thus, the image frame 400 captures an image of the patient 20 at a certain phase of a respiratory cycle. The image frame 400 may be one of the images in a sequence that also contain the image frame (e.g., image frame 300 of FIG. 3) that is used to obtain the image template of step 202.

Next, a level of similarity between the image template 308 and a portion of the input image 400 is measured (step 206). In particular, the portion 450 of the input image 400 that is at the same relative position 310 (at which the image template 308 is obtained from the image frame 300) is used to compare with the image template 308. In other words, the measure of similarity is calculated between the template and a fixed sub-area of the input image 400 (i.e., the fixed sub-area of the image frame that is used to define the template). Various techniques may be used to measure the level of similarity between the image template 308 and the portion of the input image 400. In some embodiments, the processor 14 may perform a normalized cross correlation between the image template 308 and the portion of the input image 400.

Because the image template is obtained from an image frame that is generated when the patient 20 is at a certain position (e.g., a position that may correspond with a certain phase of a respiratory cycle), if the input image (e.g., input image 400*a*) is generated when the object moving with respiration is in the same position as that associated with the image template, the resulting level of correlation would be high. On the other hand, if the input image (e.g., input image 400*b*) is generated when the portion of the patient 20 is in a different position from that associated with the image template, the resulting level of correlation would be relatively low. It should be noted that the correlation determined by the processor may or may not be normalized. If normalized correlation is used, the value of the normalized correlation (correlation coefficient) is used to represent a level of similarity between the two images. In other embodiments, instead of cross-correlation, other similarity measures may be used, such as, mutual information, absolute difference, etc.

Returning to FIG. 2, after the level of similarity is determined, the determined level of similarity is then used as a part of a time series (step 208). The above steps 204-208 are then repeated. In particular, the processor 14 obtains additional image frames (step 204), and measures levels of similarities for respective additional image frames (step 206). The image frames may be images that are generated in a sequence. For example, the image frames may be images that are generated successively one after the other. Alternatively, the image frames may be every other image, or images spaced at other intervals (e.g., every 3rd image, every 4th image, etc.) that are in the sequence. The measured levels of similarities together form a time series that can be used by the processor 14 (step 208).

Figure 5:
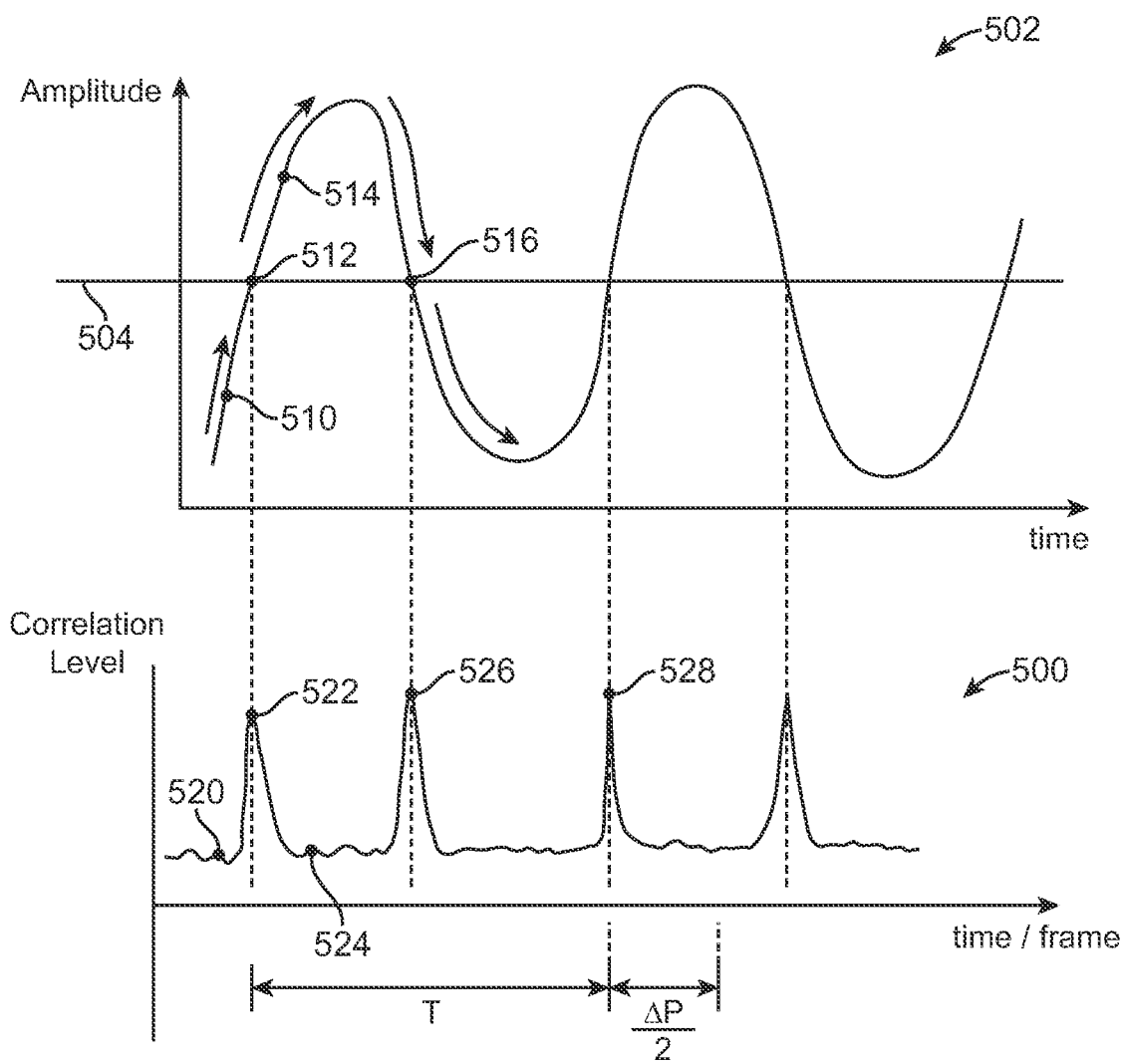
FIG. 5 illustrates an example of a breathing curve aligned with an example of a correlation graph.

FIG. 5 illustrates an example of a time series 500 of similarity values that may be generated using the method 200. In the figure, the time series 500 is aligned with a breathing chart 502 to show the relationship between various points in the time series 500 and the points in the breathing chart 502. The time series 500 includes a plurality of points representing levels of correlation between the image template and respective input image frames that are determined in step 206 of the method 200. In the illustrated example, the time series 500 is constructed by connecting the data points to form a continuous graph. In other embodiments, the data points in the time series 500 need not be connected, and the graph of the time series 500 is presented as a series of points. The breathing chart 502 illustrates a breathing pattern of the patient 20, with the x-axis representing time, and the y-axis representing amplitudes of motion (e.g., motion of chest, motion of the patient's clothes, motion of a blanket covering the patient 20, etc.) associated with the breathing. A line 504 is shown in the chart 502, wherein the line 504 represents the amplitude at which the image template is generated. As the patient 20 inhales at point 510, the image frame captured by the optical device 12 will be different from the image template, and the level of similarity between the image template and the image frame corresponding to point 510 (point 520 in time series) will be low. At point 512, the image frame captured by the optical device 12 will be the same as the image template (because they are captured when the patient 20 is in the same position), and the level of similarity between the image template and the image frame corresponding to point 512 (point 522 in time series 500) will be high. As the patient 20 continues to inhale, his/her position moves away from the position that corresponds to line 504, and as a result, the level of similarity between the image frame at point 514 and the image template is relatively low (point 524 in time series 500). The patient 20 then exhales, and when the breathing pattern reaches point 516, the image frame captured by the optical device 12 will be again the same as the image template (because they are captured when the patient 20 is in the same position), and the level of similarity between the image template and the image frame corresponding to point 516 (point 526 in time series 500) will be high.

As illustrated in the figure, the peak values (e.g., points 522, 526) in the time series 500 correlate with certain parts of a physiological motion (e.g., the parts of the breathing motion having amplitude that corresponds with line 504). Thus, the time series 500 may be used to correlate with the physiological motion of the patient 20. Also, in the illustrated example, the processor 14 may determine the period T of the patient's breathing cycle by calculating the time spacing between every other peak (e.g., between peak 522 and peak 528).

In accordance with some embodiments, the time series of similarity values may be used to determine physiological information about the patient 20. For example, in some embodiments, the time series of the measured level of similarities is analyzed by the processor 14 in real time to determine if there is a lack of motion by the patient 20. The no-motion condition can result from the patient 20 having stopped breathing, or because of a position shift that has left no moving object inside the camera field of view. Lack of motion can be detected by detecting a plurality of correlation points in the time series that form a "flat-line" configuration. In some embodiments, this is achieved by calculating the variation of the signal over a sliding time window that trails the current image frame. The length of the window can be a fixed number of seconds, or it can be an adaptive window, for example, set to two breathing cycles and updated periodically according to the latest estimate of the breathing period. The threshold value of signal variation resulting in a no-motion alert is a multiplier of the noise level in the signal. The noise level is estimated automatically by a real-time signal smoothing method. For example, if the signal 99 percentile amplitude variation over the sliding time window does not exceed a multiplier of six standard deviations of the noise, then the no-motion output alert is generated.

Figure 6:
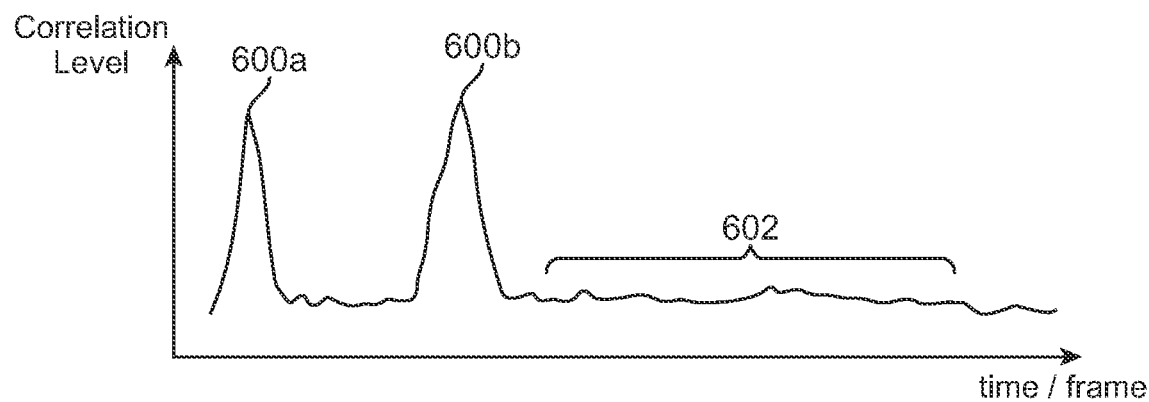
FIG. 6 illustrates another example of a correlation graph, a portion of which indicates non-motion of a subject.

FIG. 6 illustrates an example of a time series of measured level of similarities having a pattern that may be indicative of a lack of motion by the patient 20. As discussed, the time series is obtained by determining a level of similarity between the image template and a portion of each input image in a sequence. The result is a series of points with values that represent levels of correlation/similarity between respective input images (i.e., the portion within the respective input images) and the image template. In the example, the series of correlation points are connected to highlight the pattern of the series. In the illustrated example, the processor 14 keeps track of the peaks 600 that represent high correlation between the image template and the input image portions. If the processor 14 determines that there is no peak for a prescribed duration (i.e., a flat-line condition) after the last detected peak, such as the portion 602 illustrated in the example of the time series, then the processor 14 determines that there is lack of motion by the patient 20. In some embodiments, if such condition is detected, the processor 14 may generate a warning signal, such as an audio and/or a visual signal, to alert that the patient 20 is not moving. In some embodiments, the prescribed duration may be expressed as a multiplier of a breathing period BP of the patient 20, such as 2BP, 3BP, etc. In other embodiments, the prescribed duration may be an actual time value that is between 5 seconds and 24 seconds. In further embodiments, the prescribed duration may be expressed in terms of breathing period, such as any value between 2 to 4 breathing periods. Also, in some embodiments, the condition that no peak is considered detected if the level of correlation is below a prescribed level. For example, in the case of a normalized correlation, the condition that no peak is considered detected if the level of normalized correlation is below 15%. Other threshold values may also be used in other embodiments. The prescribed duration and the correlation threshold may be inputted via the user interface 18 or may be set to fixed values that are known to work for a given application.

In some cases, the noise level used in automatic threshold setting for flat-line detection can be estimated by subtracting a smoothed portion of the signal from the original signal. The smoothed signal can be obtained by an Nth order polynomial fit to the signal over a sliding window that trails the current signal sample. For example, the fitting parameters can be N=3 and a window length of 1 second. Alternatively, an adaptive window length equal to 20% of the breathing period (which is estimated in real time) can be used. The polynomial value at the current sample time represents the smoothed version of the signal. The difference between this and the original signal is observed over the same time window as the one used for flat-line detection. The RMS value of the difference can be used as the noise platform for adaptive threshold setting in flat-line detection.

Figure 7:
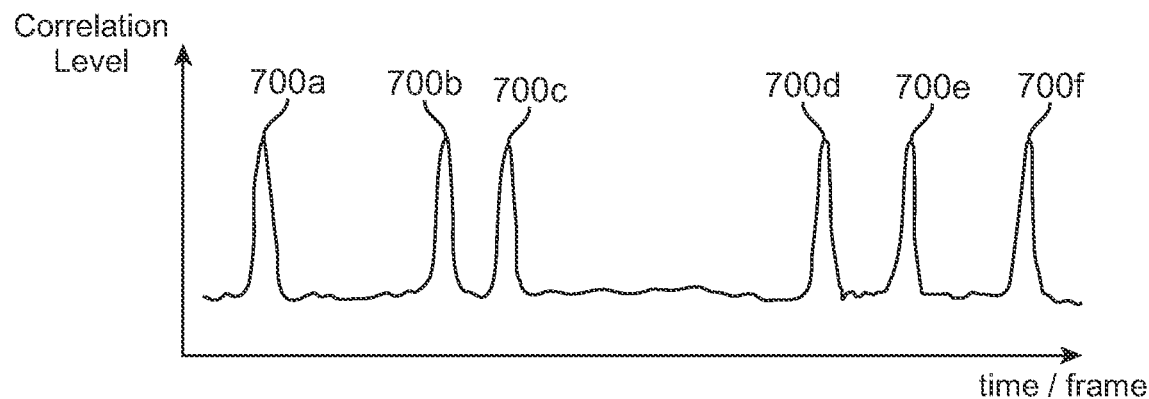
FIG. 7 illustrates another example of a correlation graph that indicates non-periodic movement of a subject.

In other embodiments, the time series of the measured level of similarities is analyzed by the processor 14 in real time to determine if there is irregularity (or lack of periodicity) in the breathing pattern of the patient 20. FIG. 7 illustrates another example of a time series of measured level of similarities having a pattern that may be indicative of lack of periodicity in the breathing of the patient 20. In the illustrated example, the processor 14 keeps track of the peaks 700 that represent high correlation between the image template and the input image portions, and the time duration between each adjacent peaks 700. If the processor 14 determines that the time durations between adjacent peaks exhibit an irregular pattern, such as the example shown in FIG. 7, then the processor 14 determines that there is lack of periodicity in the patient's breathing. In some embodiments, if such condition is detected, the processor 14 may generate a warning signal, such as an audio and/or a visual signal, to alert that the patient 20 is not breathing regularly. Alternatively, the detection of non-periodic motion by the processor 14 may indicate that the detected motion may not be breathing motion. Thus, the detection of non-periodic motion by the processor 14 may be used to guard against producing a false negative result when scene variations in the camera field of view are unrelated to the subject breathing. In some cases, the processor 14 is configured to calculate the standard deviation for the time durations between adjacent peaks (e.g., that occur within a prescribed window of time/image frames), and the time durations between adjacent peaks may be considered as exhibiting an irregular pattern if the calculated standard deviation exceeds a prescribed threshold. Criteria for determining lack of periodicity, such as the prescribed standard deviation threshold described above, may be inputted via the user interface 18.

Figure 8:
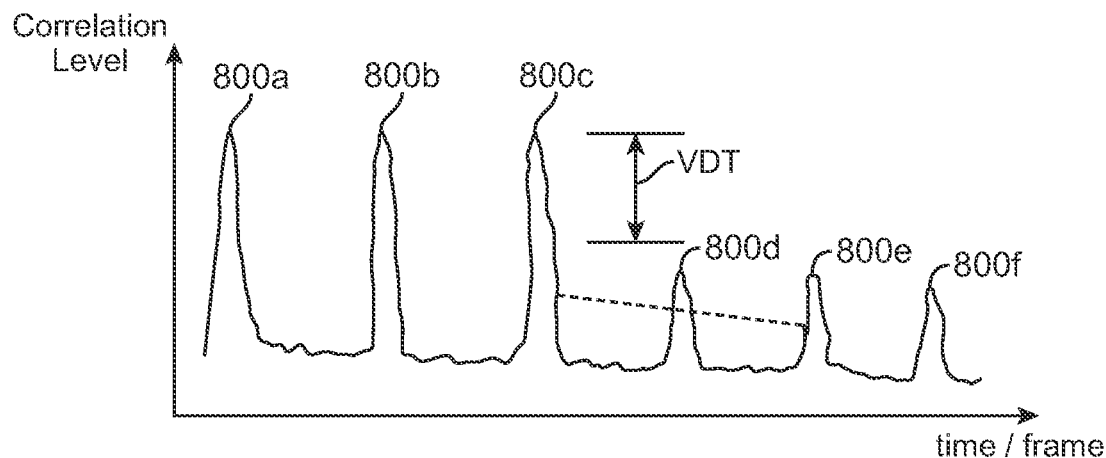
FIG. 8 illustrates another example of a correlation graph that indicates that a subject has shifted position.

In other embodiments, the time series of the measured level of similarities is analyzed by the processor 14 in real time to determine if the patient 20 has shifted in position. FIG. 8 illustrates another example of a time series of measured level of similarities having a pattern that may be indicative of a shift in position by the patient 20. In the illustrated example, the processor 14 keeps track of the peaks 800 that represent high correlation between the image template and the input image portions. If the processor 14 determines that the peak values of the correlation for a certain prescribed time/image frames are lower than those previously, such as the example shown in FIG. 8, then the processor 14 determines that the patient 20 has shifted position. In some embodiments, if such condition is detected, the processor 14 may generate a warning signal, such as an audio and/or a visual signal, to alert that the patient 20 has shifted. Alternatively, or additionally, the processor 14 may also obtain a new image template which corresponds to the new position of the patient 20. In such cases, the method 200 of FIG. 2 will be repeated to generate new time series of correlation values using the new image template, and the time series of correlation values may be used to determine physiological information about the patient 20, as described herein. An updating of the image template allows continued breathing monitoring with high sensitivity even after the patient 20 has shifted. In some embodiments, position-shift condition may be defined as the condition where signal amplitude falls below certain percentage (e.g., 20%) of the initial signal amplitude observed after a new template is acquired. In some cases, the processor 14 is configured to compare a current peak value (e.g., peak 800*d*) with a previous peak value (e.g., peak 800*c*), and if the current peak value 800*d* is lower than the previous peak value 800*c* by more than a prescribed threshold (a value-drop threshold—"VDT"), the processor 14 then continues to monitor subsequent peak values (e.g., peaks 800*e*, 800*f*). If the subsequent peak values are consistently (e.g., within a prescribed window of time/image frames) lower than the previous peak value 800*c* by more than the prescribed value-drop threshold VDT, the patient 20 may be considered as having a position shift. Criteria for determining patient's position shift, such as the prescribed value-drop threshold, and the prescribed time/image frames described above, may be inputted via the user interface 18.

Figure 9:
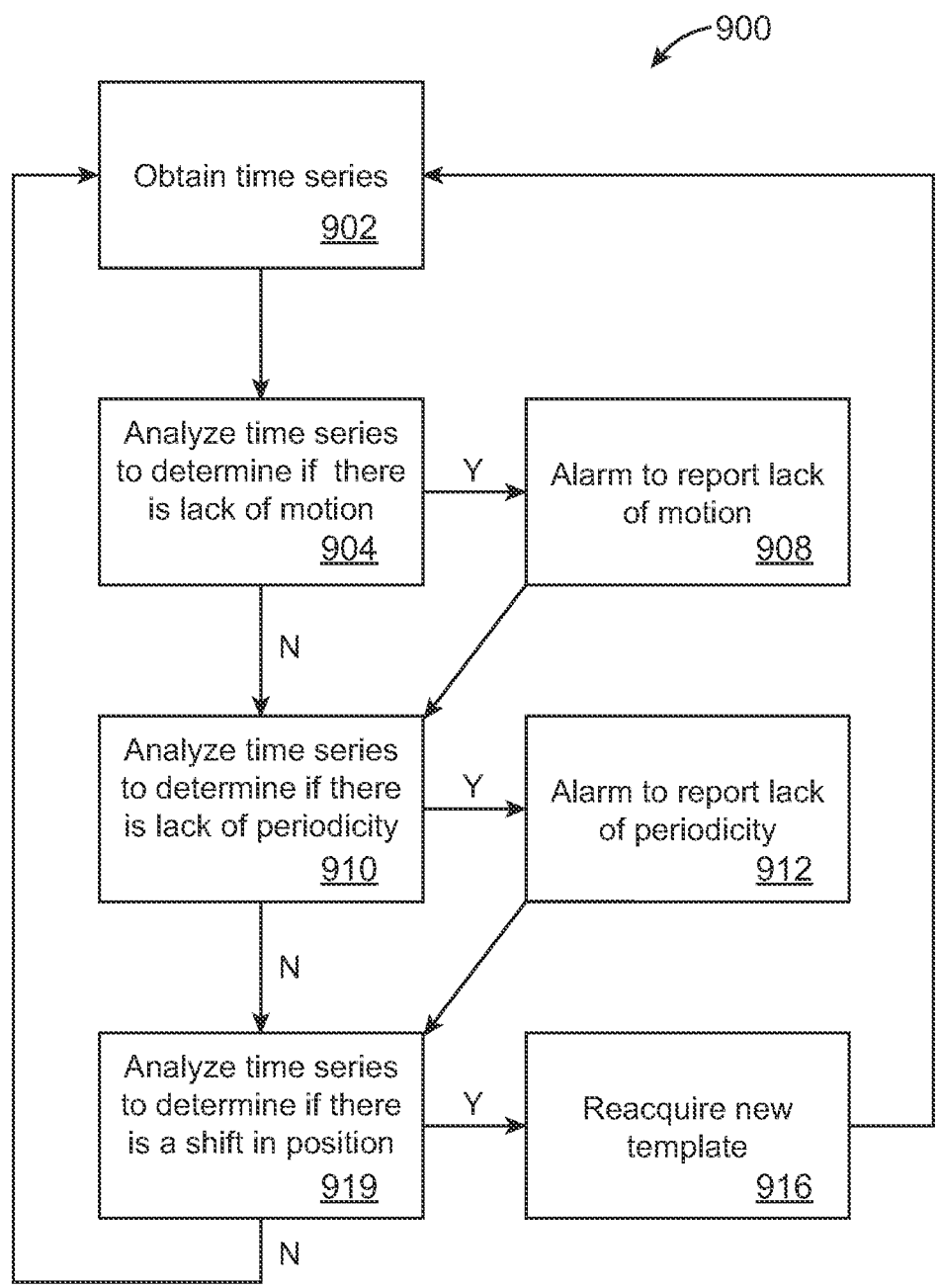
FIG. 9 illustrates a method of using a time series of correlation values to detect conditions of a patient in accordance with some embodiments.

It should be noted that the time series of measured level of similarities may be used to obtain other information regarding the patient 20 in other embodiments. Also, in other embodiments, the processor 14 may be configured to determine a combination or all of the above information (e.g., lack of motion, lack of periodicity in breathing, and/or position shift) about the patient 20. FIG. 9 illustrates a method 900 for determining physiological information about the patient 20 using a time series of correlation values in accordance with some embodiments. First, a time series of correlation values is obtained (step 902). For example, the time series of correlation values may be obtained using the method 200 of FIG. 2. Next, the processor 14 analyzes the time series to determine if there is a lack of motion by the patient 20 (step 904)—e.g., using any of the techniques described herein. If the processor 14 determines that there is a lack of motion by the patient 20, the processor 14 than generates an alarm signal to report lack of motion by the patient 20 (step 908). The alarm signal may be a signal for causing a speaker to generate audio energy, or for causing a display or LCD to generate a visual warning.

The processor 14 next analyzes the time series to determine if there is a lack of periodicity in the patient's breathing (step 910)—e.g., using any of the techniques described herein. If the processor 14 determines that there is a lack of periodicity in the patient's breathing, the processor 14 then generates an alarm signal to report lack of periodicity (step 912). Alternatively, in stead of generating an alarm the processor 14 may use the detected lack of periodicity to guard against producing a false negative result for the detection of other conditions related to breathing.

Next, the processor 14 analyzes the time series to determine if the patient 20 has shifted position (step 914)—e.g., using any of the techniques described herein. If the processor 14 determines that the patient 20 has shifted position, then the processor 14 requires a new image template—e.g., using any of the techniques described herein (step 916). Alternatively, or additionally, the processor 14 may also generate an alarm signal to report position shift by the patient 20 (step 916). In any of the embodiments described herein, different sound pitch and different colors and shapes of warning signals may be used to distinguish the type of alerts (e.g., lack of motion alert, lack of periodicity alert, patient shift alert) and the severity of the alerts (e.g., the longer the duration of lack of motion, the more severe the alert).

In some embodiments, in order to maintain sensitivity, a new image template is acquired whenever one of the above conditions (no-motion, lack of periodicity, position shift) is detected. After this updating of the image template, the newly observed signal forms the basis for position-shift detection threshold also, the detection of flat-line and periodicity start anew by resetting the adaptive algorithm parameters and signal buffers.

As illustrated by the embodiments described herein, the system 10 is advantageous in that it does not require any attachment of markers that are specially designed for image detection. It also does not require the patient 20 to wear special clothing or cover, and will work as long as the optical device 12 field of view contains sufficient objects that move with the patient's breathing, such as a blanket, sheet, etc. Also, the above described techniques for determining lack of motion, lack of periodicity, and patient's position shift are advantageous because they involve simple image processing without the need to perform complex calculation to determine actual position of the patient 20 or patient's portion. The above described techniques are also advantageous in that they do not require use of complex object discrimination algorithms to identify object(s) in an image. This is because the same region of interest in each input image is compared with the template, regardless of what object is captured within the region of interest in each input frame. The embodiments of the technique described herein is also advantageous in that it is sensitive and allows pickup of smaller motion levels, such that analysis for lack of motion, periodicity, and patient shift can be performed for much smaller motion amplitudes. Because of the template re-acquisition feature, the technique is more robust because it can keep monitoring the breathing even when the patient 20 position shifts by large amounts, as long as some portion of the patient 20 that moves with breathing remains in the optical device's 12 field of view.

It should be noted that the method 900 should not be limited to the order of steps described above, and that the steps may have different orders. For example, in other embodiments, the processor 14 may perform step 910 and/or step 914 before step 904. Also, in other embodiments, two or more steps in method 900 may be performed in parallel. For example, in other embodiments, steps 904, 910, 914 may be performed in parallel by the processor 14.

In some embodiments, the processor 14 is configured to determine physiological information about the patient 20 using the time series of similarity values in real time (e.g., at substantially the same time or shortly after the current input image is obtained). Alternatively, the processor 14 may be configured to use the time series of similarity values retrospectively.

Figure 10:
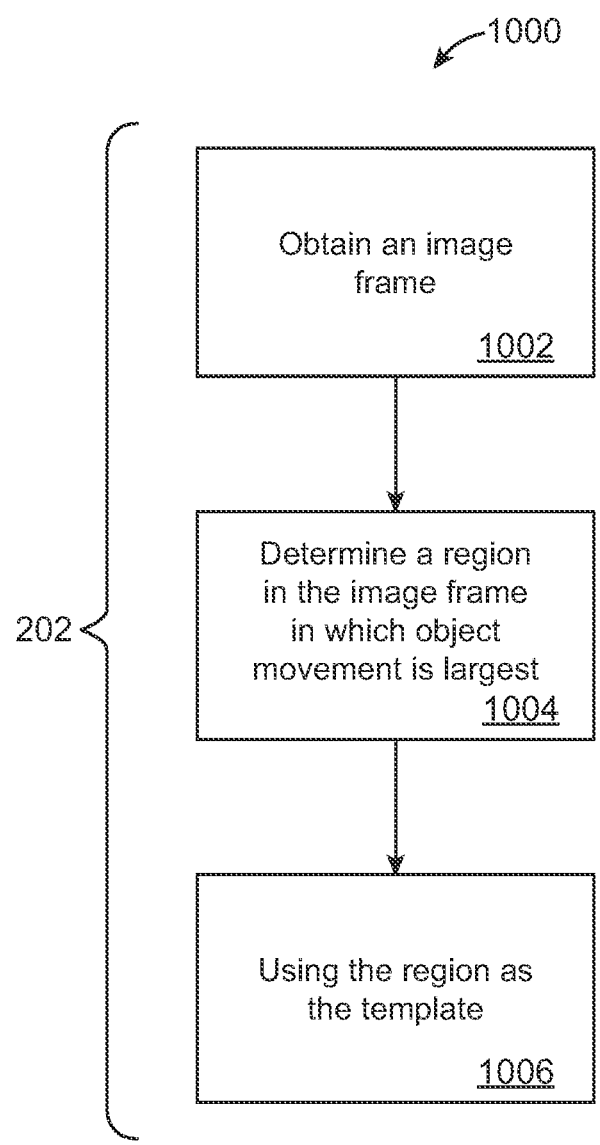
FIG. 10 illustrates a method of obtaining a template in accordance with some embodiments.

As discussed, in some embodiments, the image template in step 202 is obtained from an image within an area of an image frame in which there is patient's movement. FIG. 10 illustrates a method 1000 for determining an area in an image frame that has an image of an object captured while the object was undergoing movement in accordance with some embodiments. First, a real-time input image $I_n$ is obtained using the optical device 12 (Step 1002). The image is then analyzed to determine a region in the image that captures a moving object—e.g., a region in the image where there is object movement, or where movement is the largest (Step 1004). In the illustrated embodiments, the current input image $I_n$ is subtracted from a reference image RI to obtain a composite image $CI_n$ (i.e., $CI_n = I_n - RI$). The reference image RI may be a previously acquired image frame such as the frame just preceding the current frame. The composite image $CI_n$ is then analyzed to determine an area having an image of an object that was captured while the object was moving. If there has been object movement, the pixels in the composite image $CI_n$ should have an increase in contrast (which represents motion energy). It may be considered that there has been object movement if the contrast increase is above a certain prescribed threshold. In other embodiments, instead of using a reference image RI, an average of previously acquired input images may be used in the above method. After the region in the image that has the largest object movement is determined, the region is then used as the template (Step 1006). In some cases, the position of the region relative to the image frame is also determined and stored for later use, as described herein. In other embodiments, other techniques for obtaining the image template in step 202 may be used, and the method 1000 needs not be performed. For example, in other embodiments, the image template in step 202 may be obtained by capturing an image frame of an object that moves with a patient movement.

Figure 11:
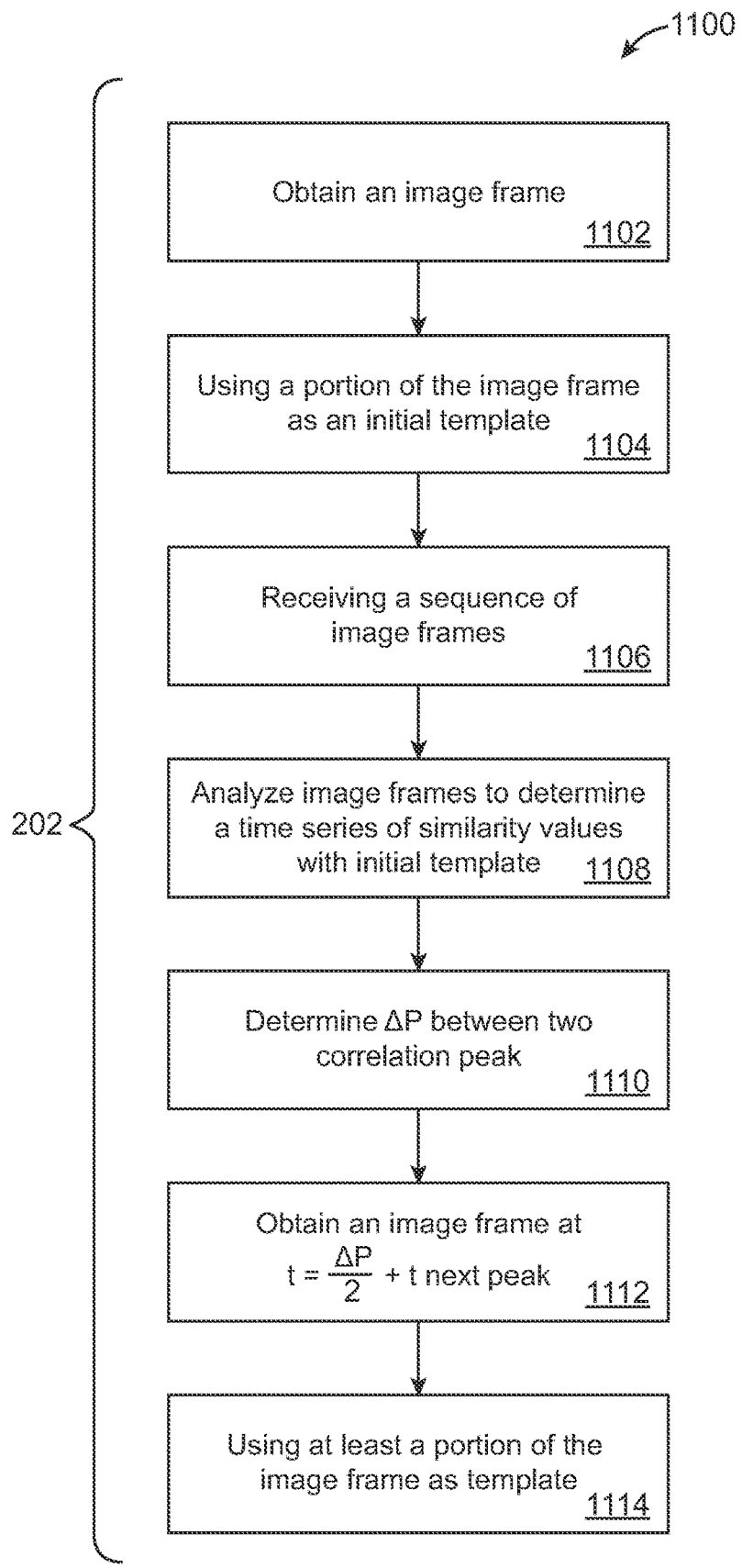
FIG. 11 illustrates another method of obtaining a template in accordance with other embodiments.

In the above embodiments, the image template is obtained when the patient 20 is at an arbitrary phase of a respiratory cycle. In other embodiments, the image template may be obtained when the patient 20 is at an end of an inhale or exhale phase. This merges the two peaks of. FIG. 5 resulting in better correspondence between the similarity measure time series and the breathing state of the subject. FIG. 11 illustrates a method 1100 for obtaining the image template when the patient 20 is at an end of an inhale or exhale phase in accordance with other embodiments. First, an image frame is obtained (step 1102), and a portion of the image frame is used as an initial image template (step 1104). The image frame for the initial image template may be acquired at any time point in the breathing cycle. Next, a plurality of image frames from a sequence is received (step 1106), and the image frames are processed to determine a time series of similarity values with the initial template (step 1108). The time series of similarity values (breathing signal) resulting from this initial template has two peaks per breathing cycle if the initial template is not acquired at the exhale-end or inhale-end point of a breathing cycle—such as the example shown in FIG. 5. Next, the processor 14 performs real time analysis of the signal to detect the two consecutive peaks and the time spacing ΔP between the two peaks (step 1110). Next, an image frame is obtained at a time that is ΔP/2 after the next detected peak (step 1112), and a new image template is obtained using a portion of the image frame (step 1114). The new image template from step 1114 is then used for subsequent signal processing (e.g., for determining lack of motion by the patient 20, lack of periodicity in the patient's breathing, position shift by the patient 20, etc.). For example, the image in the area in the image frame at which there is the greatest patient's motion may be used as the image template. Alternatively, instead of a portion of the image frame, the entire image frame from step 1112 may be used as the new image template.

Figure 12:
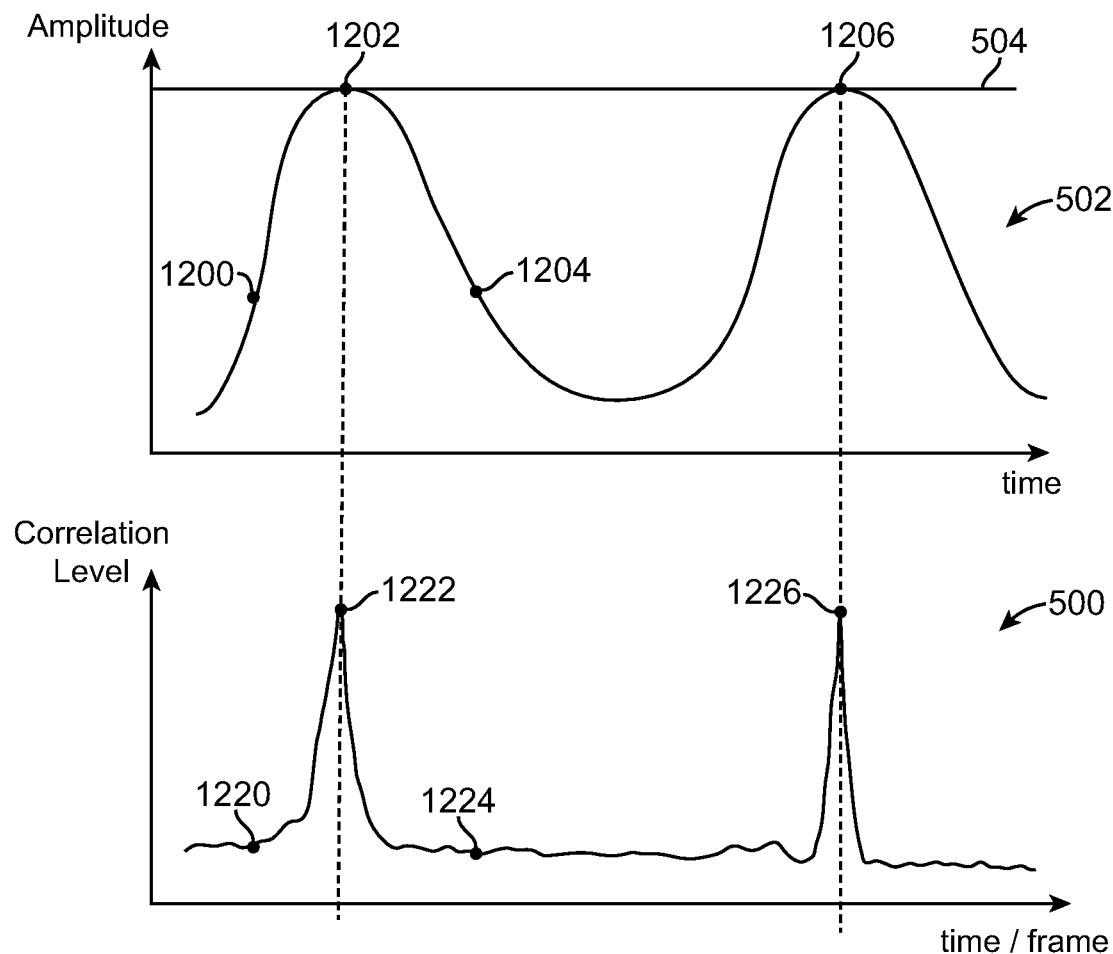
FIG. 12 illustrates that a level of correlation may be used to correlate with a certain amplitude of a physiological movement.

FIG. 12 illustrates another example of a time series 500 of similarity values that may be generated using the method 200 in which step 202 is achieved using the method 1100 of FIG. 11. In the figure, the time series 500 is aligned with a breathing chart 502 to show the relationship between various points in the time series 500 and the points in the breathing chart 502. The time series 500 includes a plurality of points representing levels of correlation between the image template and respective input image frames that are determined in step 206 of the method 200. The breathing chart 502 illustrates a breathing pattern of the patient 20, with the x-axis representing time, and the y-axis representing amplitudes of motion (e.g., motion of chest, motion of the patient's clothes, motion of a blanket covering the patient 20, etc.) associated with the breathing. A line 504 is shown in the chart 502, wherein the line 504 corresponds to the position of the patient 20 at an end of the inhale phase at which the image template is generated. As the patient 20 inhales at point 1200, the image frame captured by the optical device 12 will be different from the image template, and the level of similarity between the image template and the image frame corresponding to point 1200 (point 1220 in time series 500) will be low. At point 1202, the image frame captured by the optical device 12 will be the same as the image template (because they are captured when the patient 20 is in the same position—i.e., at the end of the inhale phase), and the level of similarity between the image template and the image frame corresponding to point 1202 (point 1222 in time series 500) will be high. As the patient 20 exhales, his/her position moves away from the position that corresponds to line 504, and as a result, the level of similarity between the image frame at point 1204 and the image template is relatively low (point 1224 in time series 500). The patient 20 then inhales again, and when the breathing pattern reaches point 1206, the image frame captured by the optical device 12 will be again the same as the image template (because they are captured when the patient 20 is in the same position—i.e., at the end of the inhale phase), and the level of similarity between the image template and the image frame corresponding to point 1206 (point 1226 in time series 500) will be high.

As illustrated in the figure, the peak values (e.g., points 1222, 1226) in the time series 500 correlate with certain parts of a physiological motion (e.g., the end of the inhale phase). Thus, the time series 500 may be used to correlate with the physiological motion of the patient 20. Also, in the illustrated example, the processor 14 may determine the period T of the patient's breathing cycle by calculating the time spacing between adjacent peak (e.g., between peak 1222 and peak 1226). Also, as illustrated in the figure, obtaining the image template when the patient 20 is at the end of the exhale phase is advantageous in that the peaks in the time series of similarity values correspond with the respective peaks (end of inhale phase) in the breathing pattern.

In other embodiments, instead of obtaining the image template when the patient 20 is at the end of the inhale phase, the image template may be obtained when the patient 20 is at the end of the exhale phase. In such cases, the peaks in the time series of similarity values will correspond with the respective valleys (end of exhale phase) in the breathing pattern.

Figure 13:
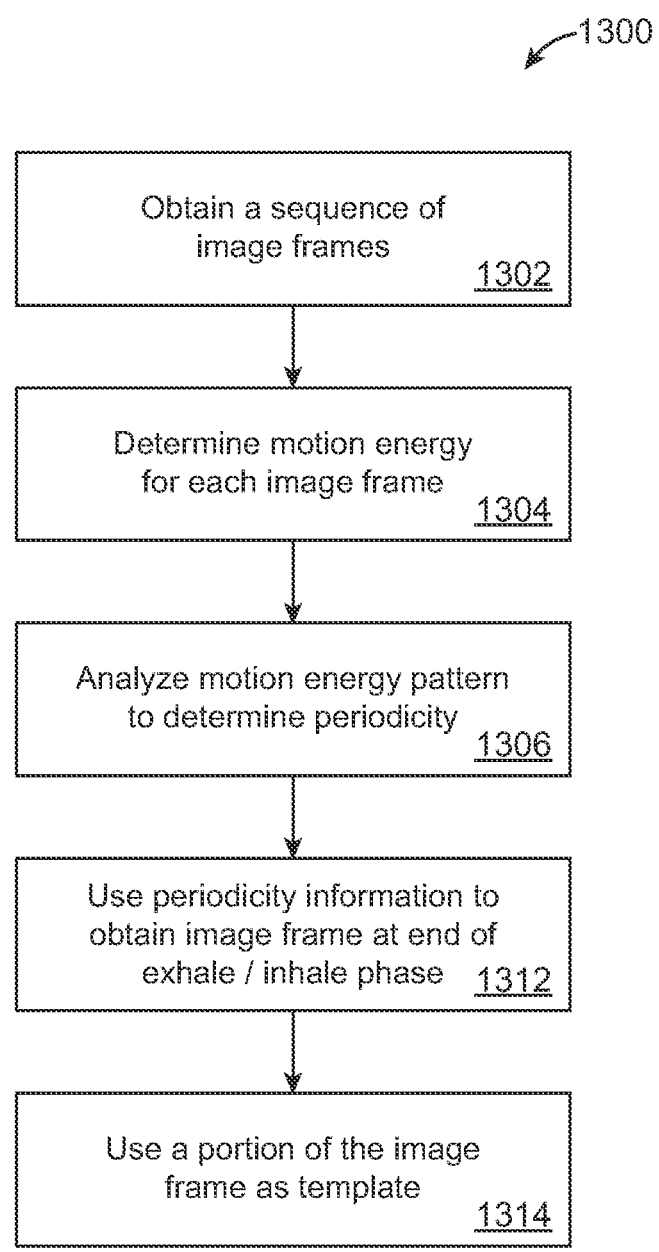
FIG. 13 illustrates another method of obtaining a template in accordance with other embodiments.

FIG. 13 illustrates another method 1300 for obtaining the image template when the patient 20 is at an end of an inhale or exhale phase in accordance with other embodiments. First, a plurality of input images is obtained using the optical device 12 (step 1302). Next, motion energy is determined for each of the input images (step 1304). In the illustrated embodiments, motion energy for each input image is determined by subtracting the current input image from a reference image, which may be, for example, a previously acquired input image. Alternatively, motion energy for each input image is determined by subtracting the current input image from an average image that is determined by taking an average of a prescribed number of previously obtained input images. The determined motion energies for respective input images are analyzed in real time as a time series to determine periodic characteristic of the patient's movement (step 1306). For example, the time series of motion energies may be used to detect time points at which the patient's motion is the least, which correspond with exhale and inhale phases of breathing but without necessarily knowing whether it is inhale or exhale. The processor then determines the time spacing ΔP between the two time points. Next, an image frame is obtained at a time that motion energy reaches a minimum indicating exhale or inhale end of breathing cycle (step 1312), and a new image template is obtained using a portion of the image frame (step 1314). The new image template from step 1312 is then used for subsequent signal processing (e.g., for determining lack of motion by the patient 20, lack of periodicity in the patient's breathing, position shift by the patient 20, etc.). For example, the image in the area in the image frame at which there is the greatest patient's motion may be used as the image template. Alternatively, instead of a portion of the image frame, the entire image frame from step 1312 may be used as the new image template.

Figure 14:
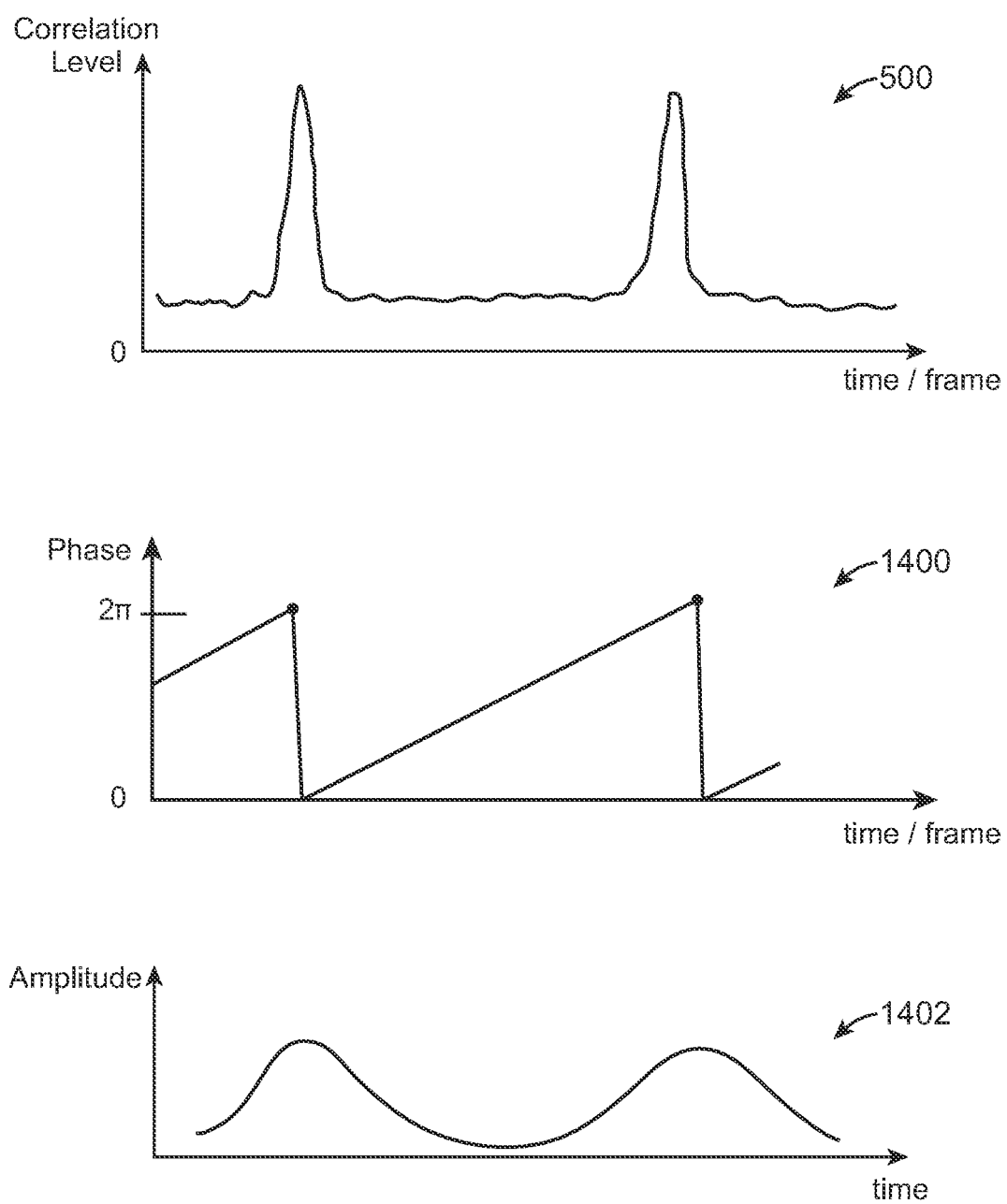
FIG. 14 illustrates that a level of correlation may be used to correlate with a phase of a physiological movement.

In the above embodiments, the peak values in the time series of similarity values correspond to certain positional value(s) associated with the patient's breathing. In other embodiments, the peak values in the time series of similarity values may correspond to other aspects associated with the patient's breathing. For example, in other embodiments, the peak values in the time series of similarity values may correspond to certain phase(s) of the patient's respiratory cycle. FIG. 14 illustrates an example of a time series 500 that is aligned with a phase chart 1400. The phase chart 1400 has a x-axis that represents time, and a y-axis that represents phase values, wherein each phase value represents a degree of completeness of a respiratory cycle. In the illustrated example, phase values range from 0° to 360°. In other embodiments, the phase values may have other values, and may be represented with different scales or units. The phase chart 1400 may be derived from an amplitude chart 1402, such as that shown in FIG. 5. As shown in FIG. 14, the peaks in the time series 500 correspond with certain phase value (e.g., 360°) in the phase chart 1400. In other examples, the peaks in the time series 500 may correspond with other phase values in the phase chart 1400.

It should be noted that the determined time series of similarity values should not be limited to the use described previously, and that the time series may also be used in other applications. In other embodiments, the determined time series may be used to gate a medical process, such as a diagnostic process in which a part of a patient is being imaged by an imaging machine, or a treatment process in which a part of the patient is being treated by a treatment device. For example, the peaks in the time series may be used to correspond to certain phase(s) of a respiratory cycle of a patient who is undergoing an imaging process (e.g., a CT imaging process, a PET process, a CT-PET process, a SPECT process, MRI procedure, etc.). Based on the detected peaks in the time series, the device that is used to obtain the image may be gated on or off so that images of the patient may be obtained at a desired phase of a respiratory cycle.

In other embodiments, instead of gating a generation of images, the time series of similarity values may be used to gate a collection of images retrospectively. In such cases, the time series is generated and recorded as the patient undergoes an imaging process. After a set of images are collected, the processor then analyzes the time series to bin the images such that images that are collected at a same phase of a respiratory cycle are grouped together. For example, the processor may associate all images that are generated at times at which the time series has similarity values of "0.9." In other embodiments, the processor may be configured to bin images based on phases of a physiological cycle. For example, the processor may be configured to associate images that are generated at a same phase (e.g., 180°), or within a same phase range (e.g., 170°-190°) of a physiological cycle.

Similarly, for treatment, the detected peaks of the time series of similarity values may be used to gate a beam on or off, and/or to gate an operation of a collimator (that is used to change a shape of the beam). In such cases, the beam has an energy that is sufficient for treating the patient, and may be a x-ray beam, a proton beam, or other types of particle beam. In some embodiments, after the processor detects a peak in the time series, the processor may be configured to activate or deactivate the beam, and/or to generate leaf sequencing signals to operate the leafs of the collimator, after a prescribed time that has lapsed since the detected peak.

Figure 15A:
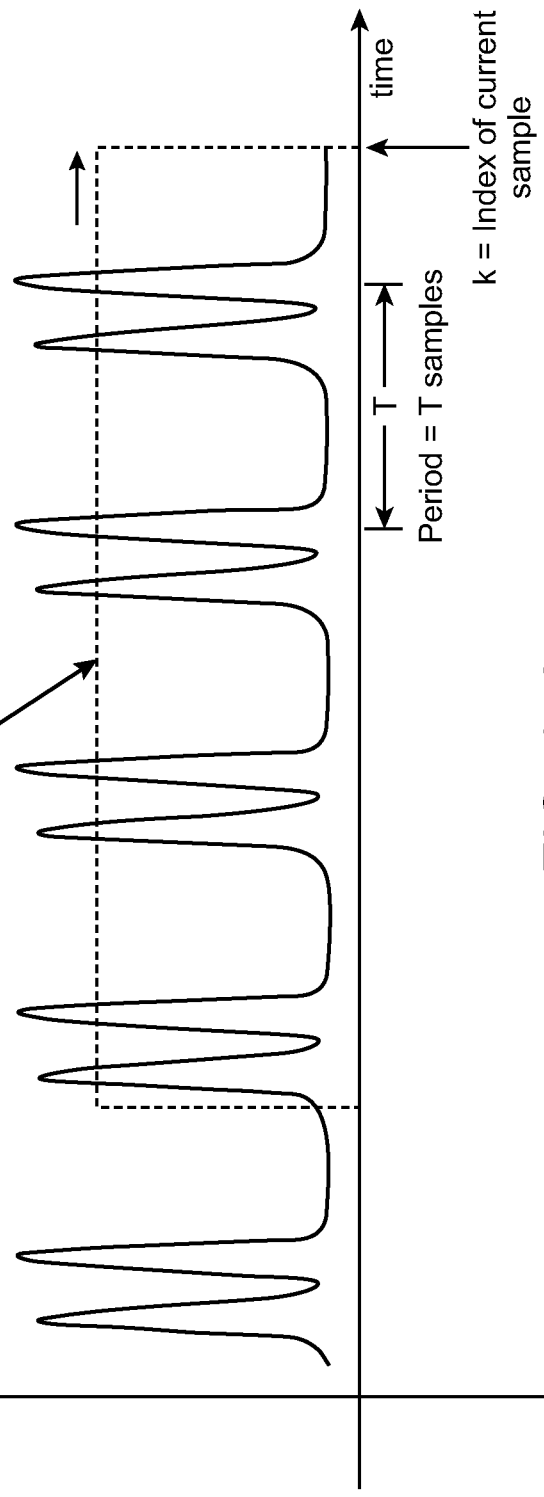
FIGS. 15A and 15B illustrate a technique for analyzing a time series of similarity values using Fourier Transform.
Figure 15B:
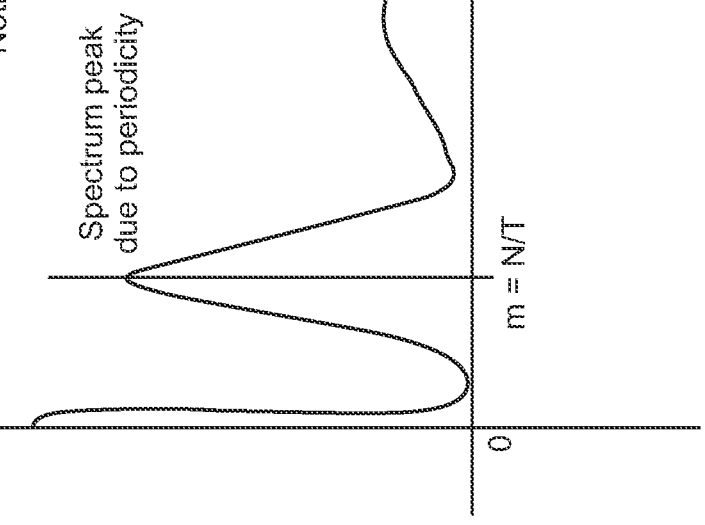

In any of the embodiments described herein, the time series of similarity values may be analyzed in the frequency domain. For example, in any of the embodiments described herein, the processor 54 may be configured to perform spectral analysis using Fourier Transform to analyze the time series of similarity values. In some cases, the processor 54 may be configured to perform spectral analysis using the time series of similarity values to detect any of the conditions described herein, such as, object motion, lack of motion, periodicity, lack of periodicity, position shift, etc. FIG. 15A illustrates an example of a time series of similarity values. As shown in the figure, when analyzing the time series in the frequency domain, a sliding window is used so that a certain amount of trailing samples S is included in the analysis. The Fourier Transform coefficients from the N motion signal samples may be calculated using the equation shown on top of FIG. 15A. FIG. 15B shows the expected power spectrum (Fourier coefficients squared) for the time series of FIG. 15A at a given time. As shown in the figure, the peak position is related to the motion period for a periodic motion. In the illustrated embodiments, a high peak-to-average ratio corresponds with a high level of periodicity, and therefore, may be used as a measure of periodicity. As shown in the figure, the average of the coefficient values (which may include the peak area) is an indication of motion amplitude irrespective of periodicity. In some embodiments, in order to establish a noise platform, the average coefficients squared outside a peak area may be calculated. As used in this specification, the term "noise platform" denotes the reference level for sensing motion from the signal. Also, the term "noise" may refer to electronic noise, which is the frame-to-frame changes of pixel values when the scene and camera are motionless. In frequency domain, if all signal spectral components (e.g., peaks in the case of periodic signals) are excluded, then the average of coefficients excluding the peak will represent the noise level. In some embodiments, instead of finding peaks and excluding them, one can look at coefficients beyond certain frequency which is known not to be anything representing physical motion, and calculate the average over those high temporal frequencies. Note that the DC component, which is the coefficient at zero frequency, is not used in the illustrated calculation because the changing component of the signal is desired to be obtained. Position shift may cause reduction in motion signal strength from its value right after acquiring a new template. The same is true if breathing motion stops. Thus, the motion signal strength may be used to detect these conditions. In some embodiments, the noise platform described above may be used to set the threshold for these measures.

Computer System Architecture

Figure 16:
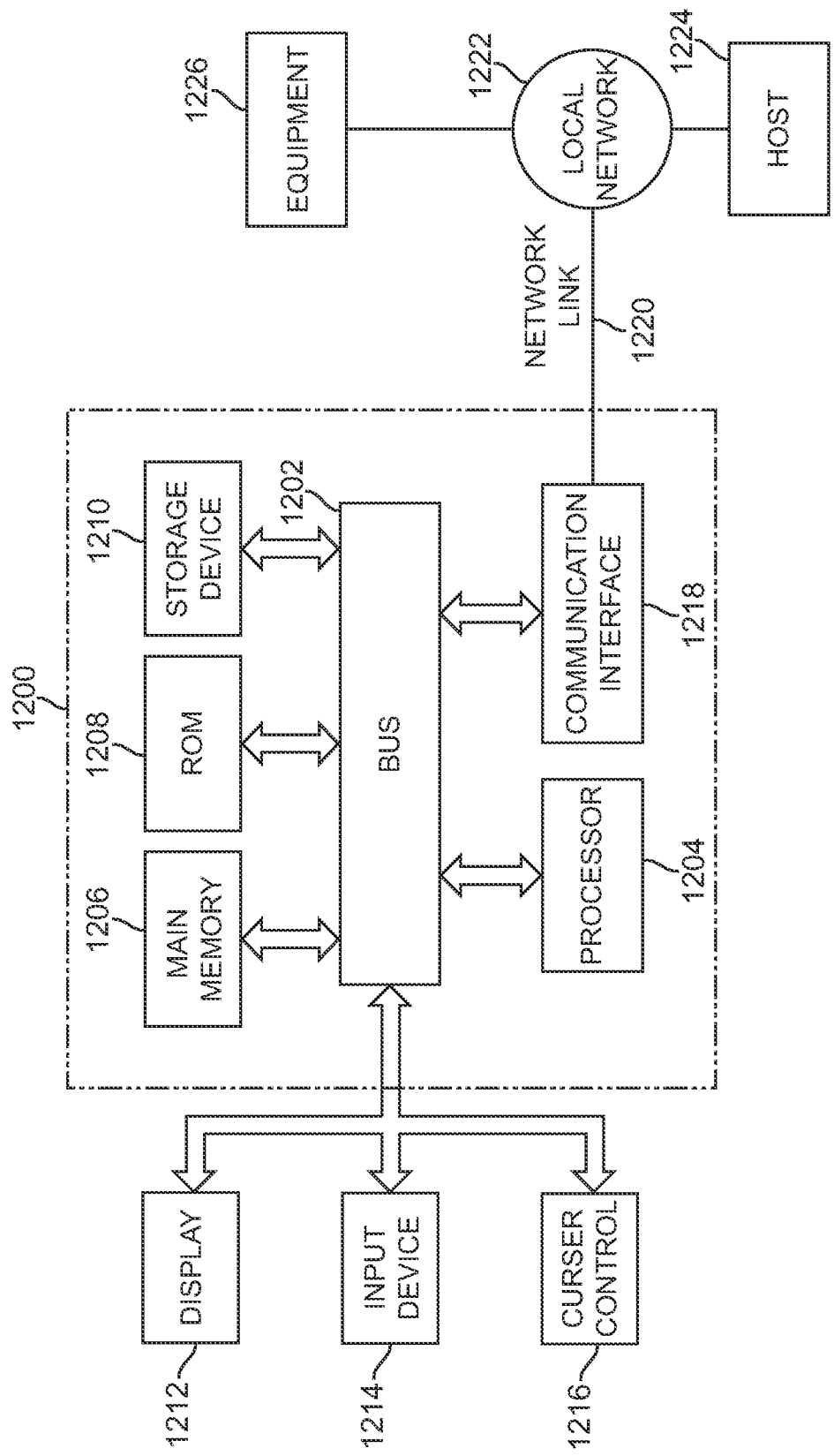
FIG. 16 is a block diagram of a computer system architecture, with which embodiments described herein may be implemented.

FIG. 16 is a block diagram that illustrates an embodiment of a computer system 1500 upon which an embodiment of the invention may be implemented. Computer system 1500 includes a bus 1502 or other communication mechanism for communicating information, and a processor 1504 coupled with the bus 1502 for processing information. The processor 1504 may be an example of the processor 54 of FIG. 1, or another processor that is used to perform various functions described herein. In some cases, the computer system 1500 may be used to implement the processor 54. The computer system 1500 also includes a main memory 1506, such as a random access memory (RAM) or other dynamic storage device, coupled to the bus 1502 for storing information and instructions to be executed by the processor 1504. The main memory 1506 also may be used for storing temporary variables or other intermediate information during execution of instructions to be executed by the processor 1504. The computer system 1500 further includes a read only memory (ROM) 1508 or other static storage device coupled to the bus 1502 for storing static information and instructions for the processor 1504. A data storage device 1510, such as a magnetic disk or optical disk, is provided and coupled to the bus 1502 for storing information and instructions.

The computer system 1500 may be coupled via the bus 1502 to a display 1512, such as a cathode ray tube (CRT), for displaying information to a user. An input device 1514, including alphanumeric and other keys, is coupled to the bus 1502 for communicating information and command selections to processor 1504. Another type of user input device is cursor control 1516, such as a mouse, a trackball, or cursor direction keys for communicating direction information and command selections to processor 1504 and for controlling cursor movement on display 1512. This input device typically has two degrees of freedom in two axes, a first axis (e.g., x) and a second axis (e.g., y), that allows the device to specify positions in a plane.

The computer system 1500 may be used for performing various functions (e.g., calculation) in accordance with the embodiments described herein. According to one embodiment, such use is provided by computer system 1500 in response to processor 1504 executing one or more sequences of one or more instructions contained in the main memory 1506. Such instructions may be read into the main memory 1506 from another computer-readable medium, such as storage device 1510. Execution of the sequences of instructions contained in the main memory 1506 causes the processor 1504 to perform the process steps described herein. One or more processors in a multi-processing arrangement may also be employed to execute the sequences of instructions contained in the main memory 1506. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1504 for execution. Such a medium may take many forms, including but not limited to, non-volatile media, volatile media, and transmission media. Non-volatile media includes, for example, optical or magnetic disks, such as the storage device 1510. Volatile media includes dynamic memory, such as the main memory 1506. Transmission media includes coaxial cables, copper wire and fiber optics, including the wires that comprise the bus 1502. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1504 for execution. For example, the instructions may initially be carried on a magnetic disk of a remote computer. The remote computer can load the instructions into its dynamic memory and send the instructions over a telephone line using a modem. A modem local to the computer system 1500 can receive the data on the telephone line and use an infrared transmitter to convert the data to an infrared signal. An infrared detector coupled to the bus 1502 can receive the data carried in the infrared signal and place the data on the bus 1502. The bus 1502 carries the data to the main memory 1506, from which the processor 1504 retrieves and executes the instructions. The instructions received by the main memory 1506 may optionally be stored on the storage device 1510 either before or after execution by the processor 1504.

The computer system 1500 also includes a communication interface 1518 coupled to the bus 1502. The communication interface 1518 provides a two-way data communication coupling to a network link 1520 that is connected to a local network 1522. For example, the communication interface 1518 may be an integrated services digital network (ISDN) card or a modem to provide a data communication connection to a corresponding type of telephone line. As another example, the communication interface 1518 may be a local area network (LAN) card to provide a data communication connection to a compatible LAN. Wireless links may also be implemented. In any such implementation, the communication interface 1518 sends and receives electrical, electromagnetic or optical signals that carry data streams representing various types of information.

The network link 1520 typically provides data communication through one or more networks to other devices. For example, the network link 1520 may provide a connection through local network 1522 to a host computer 1524 or to equipment 1526 such as a radiation beam source or a switch operatively coupled to a radiation beam source. The data streams transported over the network link 1520 can comprise electrical, electromagnetic or optical signals. The signals through the various networks and the signals on the network link 1520 and through the communication interface 1518, which carry data to and from the computer system 1500, are exemplary forms of carrier waves transporting the information. The computer system 1500 can send messages and receive data, including program code, through the network(s), the network link 1520, and the communication interface 1518.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the term "processor" should not be limited to a device having only one processing unit, and may include a device or system that has more than one processing units/processors. Thus, the term "processor" may refer to a single processor or a plurality of processors. Also, the term "image" should not be limited to image that is actually displayed, and may refer to image data or undisplayed image that is capable of being presented in an image form. Further, the term "patient" should not be limited to a person or animal that has a medical condition, and may refer to a healthy person or animal. In addition, any discussion herein with reference to an image of the patient or patient portion may refer an image of the patient (or patient portion) itself, the clothing that the patient is wearing, and/or the blanket that is covering the patient. Thus, an image of the patient or patient portion should not be limited to an image of the patient or patient portion itself. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:
1. A method comprising:
digitally obtaining a first image of an object;
digitally obtaining a second image of the object;
digitally processing the first and second images to determine a first level of similarity between the first and second images, wherein the first level of similarity comprises a similarity value derived using a two-dimensional array of pixel values of the first image and a two-dimensional array of pixel values of the second image;
obtaining a third image of the object; and
digitally processing the first and third images to determine a second level of similarity between the first and third images, wherein the second level of similarity comprises a similarity value derived using the two-dimensional array of pixel values of the first image and a two-dimensional array of pixel values of the third image, the second level of similarity being different from the first level of similarity;

wherein the first level of similarity and the second level of similarity form a time series, the first level of similarity between the first and second images representing a first phase of a physiological cycle of a patient, the second level of similarity between the first and third images representing a second phase of the physiological cycle of the patient, the physiological cycle being a respiratory cycle;

wherein the method further comprises electronically processing the time series by a processing unit to analyze the time series, wherein the time series is analyzed to determine whether one or more pre-defined criteria are satisfied for detecting and/or characterizing motion, and wherein the act of electronically processing the time series comprises using the first level of similarity as the first phase of the physiological cycle; and wherein the method further comprises:
determining a first time point $t_1$;
determining a second time point $t_2$; and
determining a period T that is between the first and second time points;
wherein the first image is obtained at a time that is a fraction of the period T after a detected peak point.

2. The method of claim 1, wherein the time series is electronically processed by the processing unit for determining whether there is a lack of motion by the patient.

3. The method of claim 2, wherein the time series is electronically processed by the processing unit for determining whether there is a lack of motion by the patient comprises determining a plurality of points within a duration in the time series that have values below a prescribed threshold.

4. The method of claim 3, wherein the duration is greater than a respiratory period of the patient.

5. The method of claim 1, wherein the time series is electronically processed by the processing unit for determining whether there is a lack of periodicity in a motion by the patient.

6. The method of claim 5, wherein the act of determining whether there is a lack of periodicity in a motion by the patient comprises determining whether the time series exhibits an irregular pattern.

7. The method of claim 1, wherein the time series is electronically processed by the processing unit for determining whether the patient has shifted in position.

8. The method of claim 7, wherein the act of determining whether the patient has shifted in position comprises determining a plurality of points within a duration in the time series that have values below a prescribed threshold.

9. The method of claim 1, wherein the time series is electronically processed by the processing unit for determining whether a motion of the object is related to breathing.

10. The method of claim 1, wherein the process further comprises generating a signal for providing an alarm that indicates the determined state of the patient.

11. The method of claim 1, further comprising detecting and/or characterizing motion without determining an actual position of the patient.

12. The method of claim 1, wherein the act of digitally processing the first and second images to determine the first level of similarity between the first and second images does not require a detection of a marker specifically designed to be detected by an imaging device.

13. The method of claim 1, wherein the act of digitally processing the first and second images to determine the first level of similarity between the first and second images does not require a performance of image recognition to identify the object in the second image.

14. The method of claim 1, wherein the patient does not have a marker that is specifically designed to be detected by an imaging device.

15. The method of claim 1, wherein the first and second images are obtained using a camera.

16. The method of claim 1, wherein the first and second images are obtained using a radiation machine.

17. The method of claim 1, wherein the object comprises at least a portion of a blanket.

18. The method of claim 1, wherein the object comprises at least a portion of the patient's clothes.

19. The method of claim 1, wherein the object is a part of the patient.

20. The method of claim 1, wherein the first image is a subset of a first image frame.

21. The method of claim 20, wherein the second image is a subset of a second image frame, and wherein a position of the first image in the first image frame is the same as a position of the second image in the second image frame.

22. The method of claim 20, further comprising obtaining the first image frame, wherein the first image is obtained by:
determining a portion in the first image frame, wherein the portion of the first image frame contains an image of a portion of the object that was undergoing a relatively high motion when the first image frame was obtained; and
using the portion as the first image.

23. The method of claim 20, further comprising obtaining the first image frame, wherein the first image frame is obtained when the patient is at an end of an exhale motion.

24. The method of claim 20, further comprising obtaining the first image frame, wherein the first image frame is obtained when the patient is at an end of an inhale motion.

25. The method of claim 1, further comprising obtaining a new image for use as the first image when it is determined that the patient has shifted position.

26. The method of claim 1, wherein the act of electronically processing the time series comprises performing a spectral analysis.

27. The method of claim 26, wherein the spectral analysis is performed to detect position shift, lack of periodicity, or lack of motion.

28. The method of claim 1, wherein the similarity value of the first level of similarity comprises a correlation value determined by performing a correlation between the first and second images.

29. The method of claim 1, wherein the similarity value of the first level of similarity indicates a degree of two-dimensional similarity between the first and second images.

* * * * *